United States Patent [19]

Gething et al.

[11] Patent Number: 5,041,376
[45] Date of Patent: Aug. 20, 1991

[54] METHOD FOR IDENTIFYING OR SHIELDING FUNCTIONAL SITES OR EPITOPES OF PROTEINS THAT ENTER THE EXOCYTOTIC PATHWAY OF EUKARYOTIC CELLS, THE MUTANT PROTEINS SO PRODUCED AND GENES ENCODING SAID MUTANT PROTEINS

[75] Inventors: Mary J. Gething; Joseph F. Sambrook; Patricia Gallagher, all of Dallas, Tex.

[73] Assignees: The Board of Regents of the University of Texas System, Austin, Tex.; Cold Spring Harbor Laboratory, Cold Spring Harbor, N.Y.

[21] Appl. No.: 282,165

[22] Filed: Dec. 9, 1988

[51] Int. Cl.$^5$ .................... C12N 15/00; C12N 5/00; G01N 33/53

[52] U.S. Cl. .................... 435/172.3; 435/172.1; 435/240.2; 435/7.21; 435/7.6; 935/50; 935/76

[58] Field of Search .................. 435/70.3, 7, 172.1, 435/172.3, 240.2, 240.4, 254; 935/10, 50

[56] References Cited

FOREIGN PATENT DOCUMENTS 63-20083  9/1988  Japan .

OTHER PUBLICATIONS

Guan et al. (1985), "Glycosylation Allows Cell-Surface Transport of a Secretory Protein", Cell, vol. 42, pp. 489-496.
Dixon et al. (1987), "Structural Features for Ligand Binding to $\beta$-ar", Embo J., vol. 6, pp. 3269-3275.
Skehel et al. (1984), "A·Carbohydrate Side Chain on Hemoglutinins . . . Inhibits Recognition by Antibody", PNAS, vol. 81, pp. 1779-1783.
1984 Cold Spring Harbor Annual Report (Aug. 1985), pp. 65-77.
J. Cell. Biochem., Supp. 11A, p. 274, Abstract E215.
J. Cell. Biochem., Supp. 11A, p. 248, Abstract E019.
Gallagher, P. et al., J. Cell. Biol., 107:2059-2073 (1988).

Primary Examiner—Robin L. Teskin
Assistant Examiner—Richard Lebovitz
Attorney, Agent, or Firm—Sughrue, Mion, Zinn Macpeak & Seas

[57]    ABSTRACT

The present invention relates to a method for identifying or shielding functional sites or epitopes of proteins that enter the exocytotic pathway of eukaryotic cells (transportable proteins) by the addition of supernumerary N-linked oligosaccharide side chains at chosen sites on the surface thereof using oligonucleotide mutagenesis. The present invention also relates to mutant transportable proteins having supernumerary N-linked oligosaccharide side chains which shield functional sites or epitopes; and genes which encode the same.

6 Claims, 4 Drawing Sheets

FIG. 1B

| NAME | SEQUENCE OF WILD-TYPE | SEQUENCE OF MUTANT |
|---|---|---|
| XHA-46+ | Ser-Ser-Thr<br>TCC-TCA-ACG | Asn-Ser-Thr<br>AAC-TCA-ACG |
| XHA-54A+ | Asn-Pro-His<br>AAT-CCT-CAT | Asn-Pro-Thr<br>AAT-CCT-ACT |
| XHA-54B+ | Asn-Pro-Thr<br>AAT-CCT-ACT | Asn-Gly-Thr<br>AAT-GGT-ACT |
| XHA-188+ | Asn-Gln-Glu<br>AAC-CAA-GAA | Asn-Gln-Ser<br>AAC-CAA-ACA |
| XHA-225+ | Gly-Leu-Ser<br>GGT-CTG-TCT | Asn-Leu-Ser<br>AAT-CTG-TCT |
| XHA-476+ | Ala-Cys-Ile<br>GCT-TGC-ATA | Asn-Cys-Thr<br>AAT-TGC-ACA |

MUTAGENIC OLIGONUCLEOTIDES

XHA-46+ 5' CCC CGT TGA G$\underline{T}$T GCT CTG AA3'

XHA-54A+ 5' AAG GAT TCG A$\underline{G}$T A$\underline{G}$G ATT GT3'

XHA-54B+ 5' AAG GAT TCG AGT A$\underline{CC}$ ATT GT3'

XHA-188+ 5' GCT GGT TTG TGT TTG GTT CG3'

XHA-225+ 5' ACT AGA CAG A$\underline{T}$T CCT TAC CC3'

XHA-476+ 5' TCT GAT TGA CTC TGT GCA A$\underline{T}$T GTT GTC ACA3'

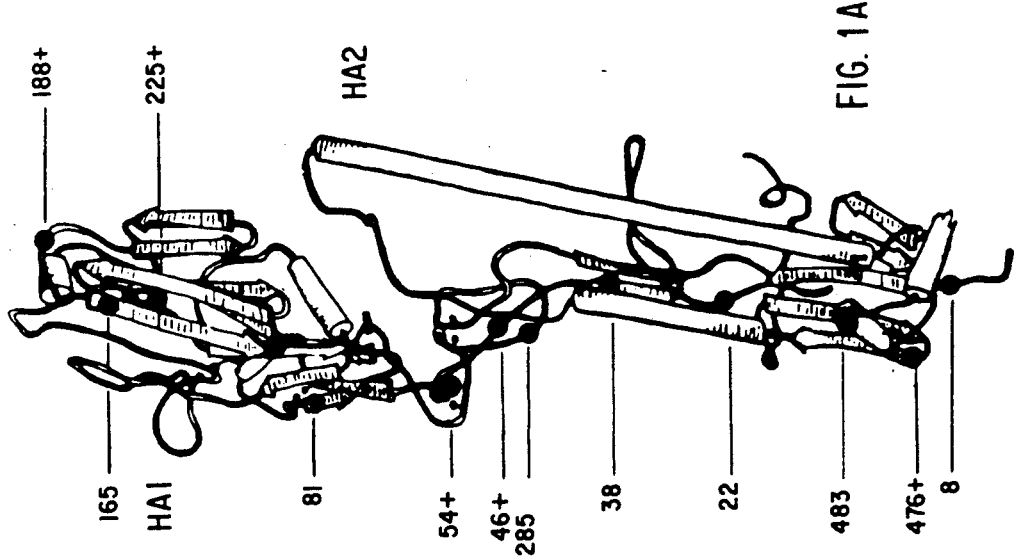

225+
GLY.LEU.SER ➔ ASN.LEU.SER
-Site not glycosylated
(steric interference from Trp222?)
- - Wild-type phenotype for transport and biological activities
-Antigenic epitopes (37°C):
$A^+, B^+, C^+, D^+$
-Antigenic epitopes (30°C):
$A^+, B^+, C^+, D^+$ 188+
ASN.GLN.GLU ➔ ASN.GLN.SER
-Site glycosylated
-Sialic acid receptor site shielded (Erythrocyte binding negative; cell fusion is positive)
-Transport slow at 37°C (conformation is more "open")
-Transport blocked at 42°C
-Antigenic epitopes (37°C):
$A^+, B^{+/-}, C^+, D^-$
-Antigenic epitopes (30°C):
$A^+, B^+, C^+, D^+$ 54B+
ASN.PRO.HIS ➔ ASN.GLY.THR
-Site glycosylated
-Transport slow at 37°C
-Transport blocked at 42°C
-Antigenic epitopes (37°C):
$A^+, B^+, C^-, D^-$
-Antigenic epitopes (30°C):
$A^+, B^+, C^-, D^+$ Intermediate $54A^+$ ASN.PRO.THR
-Not glycosylated, has similar ts phenotype
-Antigenic epitopes (37°C):
$A^+, B^+, C^+, D^-$
-Antigenic epitopes (30°C):
$A^+, B^+, C^+, D^+$ 476+
ALA.CYS.ILE ➔ ASN.CYS.THR
-Site glycosylated
-Blocked in ER at 37°C
(unfolded, protease sensitive)
-Transports to plasma membrane in folded, biologically active form at 30°C
-Antigenic epitopes (37°C):
$A^+, B^+, C^+, D^-$
-Antigenic epitopes (30°C)
$A^+, B^+, C^+, D^+$ 46+
SER.SER.THR ➔ ASN.SER.THR
-Site glycosylated
-Wild-type phenotype for transport and biological activities
-Not temperature sensitive
-Antigenic epitopes (37°C):
$A^+, B^+, C^+, D^+$
-Antigenic epitopes (30°C):
$A^+, B^+, C^+, D^+$

FIG. 3B

| | |
|---|---|
| Sequence of wild-type t-PA | -Gln-Ala-Leu-Tyr-Phe-Ser- |
| Corresponding coding sequence | -CAG-GCC-CTG-TAC-TTC-TCA- |
| Mutagenic oligonucleotide | 5'AG-GCC-CTG-AAC-TTC-TCA3' |
| Sequence of mutant t-PA67+ | -Gln-Ala-Leu-Asn-Phe-Ser- |

METHOD FOR IDENTIFYING OR SHIELDING FUNCTIONAL SITES OR EPITOPES OF PROTEINS THAT ENTER THE EXOCYTOTIC PATHWAY OF EUKARYOTIC CELLS, THE MUTANT PROTEINS SO PRODUCED AND GENES ENCODING SAID MUTANT PROTEINS

FIELD OF THE INVENTION

The present invention relates to a method for identifying or shielding functional sites or epitopes of proteins that enter the exocytotic pathway of eukaryotic cells (transportable proteins) by the addition of supernumerary N-linked oligosaccharide side chains at chosen sites on the surface thereof using oligonucleotide mutagenesis. The present invention also relates to mutant transportable proteins having supernumerary N-linked oligosaccharide side chains which shield functional sites or epitopes; and genes which encode the same.

BACKGROUND OF THE INVENTION

I. N-linked Oligosaccharide Side Chains

The function of N-linked oligosaccharide side chains that are covalently attached to the majority of eukaryotic secretory and membrane proteins is not yet fully understood. It has been suggested that the N-linked oligosaccharide side chains play a variety of roles including (i) maintenance of the structure and stability of the glycoproteins: (ii) directing the transport of glycoproteins to various subcellular compartments both after biosynthesis and for degradation: and (iii) recognition functions leading to specific adhesion of cells and tissue organization during development or neoplasia (Gibson, R. et al, *Trends Biol. Sci.*, 5:290–293 (1980); Hughes, R. C. et al. *Trends Biochem. Sci.*, 6:228–230 (1981); Pollack, L. et al, *J. Cell. Biol.*, 97:293–300 (1983); Elbein. A. D., *Trends Biochem. Sci.*, 6:219–221 (1981); and Elbein, A. D., *Annu. Rev. Biochem.*, 56:497–534 (1987)).

Studies using drugs that are specific inhibitors of the addition or modification of N-linked oligosaccharide side chains have been performed in attempts to define the functional roles of these carbohydrate moieties (Elbein. A. D., *Annu. Rev. Biochem.*, 56:497–534 (1987)). Further, the advent of recombinant DNA technology has facilitated studies involving the removal of individual glycosylation sites using oligonucleotide mutagenesis (Machamer, C. E. et al, *Mol. Cell Biol.*, 5:3074–3083 (1985); Miyazaki, J. et al, *J. Exp. Med.*, 163:856–871 (1986); Santos-Aguado, J. et al, *Molec. and Cell Biol.*, 7:982–990 (1987); Guan. J. et al, *J. Biol. Chem.*, 263:5306–5313 (1988); Matzuk, M. M. et al, *J. Cell Biol.*, 106:1049–1059 (1988)). The majority of these investigations have indicated that N-linked oligosaccharide side chains play a role in glycoprotein structure and stability, with the structure and stability of different glycoproteins being more or less dependent on the presence of their carbohydrate moieties (Elbein, A. D., *Annu. Rev. Biochem.*, 56:497–534 (1987)).

In experiments aimed at determining whether oligosaccharides play a direct role in promoting protein transport to the cell surface, oligonucleotide-directed mutagenesis has been used to introduce glycosylation sites at novel positions on nascent polypeptides. In some of these cases, the extra oligosaccharides promoted the intracellular transport of mutant proteins that were previously blocked in transport along the secretory pathway (Guan, J. et al, *Cell*, 42:489–496 (1985); Machamer, C. E. et al, *J. Biol. Chem.*, 263:5948–5954 (1988); and Machamer, C. E. et al, *J. Biol. Chem.*, 263:5955–5960 (1988)). Because the three-dimensional structures of these proteins were not known, it was not possible to predict whether the novel oligosaccharide side chains were attached at positions normally located on the surface or within the interior of the wild-type protein.

II. Identification of Functional Sites or Epitopes

Current approaches to the identification and localization of functional sites or epitopes on proteins involve complex and lengthy procedures. For example, chemical reagents that modify specific types of amino acids have been screened for those that cause inhibition of functional activity so as to identify and locate functional sites and epitopes on the proteins (Gething, M. J. et al, *Eur. J. Biochem.*, 78:111–117 (1977); Trexler. M., *J. Biol. Chem.*, 257:7401–7406 (1982)). Alternatively, proteins that interact with the functional site or epitope of interest have been cross-linked so as to identify and locate functional sites and epitopes on the proteins (Pilch, P. F. et al, *J. Biol. Chem.*, 254:3375–3380 (1979); and Swenson, E. et al, *Fibrin.*, 2:107 (1988)). In both types of experiments, protein isolation and amino acid sequence analysis are required to locate the site of modification in the protein sequence. Hence, these procedures are disadvantageous because they are lengthy and require large quantities of protein. That is, many proteins that are of great interest for medical or technological purposes are found only in minute quantities which are unsuitable for analysis by classical protein chemistry procedures.

Monoclonal antibodies directed against proteins can be raised and screened to identify those which can "block" the function of interest (Morgan, D. O. et al, *Biochem.*, 25:1364–1371 (1986); and MacGregor, I. R. et al, *Thrombosis & Haemostasis*, 53:45–50 (1985)). However, this procedure does not identify the location on the protein recognized by the monoclonal antibody. i.e., extensive additional work. e.g., sequencing (at the gene or protein level) of mutants that no longer bind the appropriate monoclonal antibody is still required to localize the functional sites or epitopes (Daniels, R. S. et al, *EMBO J.*, 6:1459–1465 (1987); and Rogers, G. N. et al, *Nature*, 304:76–78 (1983)).

Nucleotide substitutions directing single amino acid changes can be introduced into the gene encoding a protein of interest in order to identify its functional sites or epitopes. Following expression in the appropriate cell type, the mutants can be tested for abolition of functional or epitopic activity in the absence of generalized folding defects.

When a selection scheme can be devised for the activity of the protein of interest, non-functional mutant proteins can be identified by random mutagenesis followed by genetic screening (Hecht, M. H. et al, *Proc. Natl. Acad. Sci. U.S.A.*, 80:2676–2680 (1983); and Shortle, D. et al, *Genetics*, 110:539–555 (1985)). Mutants can then be tested for the absence of generalized folding defects. However, identification of the position of the mutation still requires sequence analysis of the mutant gene or protein (Hecht, M. H. et al, *Proc. Natl. Acad. Sci. U.S.A.*, 80:2676–2680 (1983); and Shortle, D. et al, *Genetics*, 110:539–555 (1985)). Although this procedure is less time consuming than those described above, suitable selection schemes are not generally available for all proteins of interest.

When a selection scheme is not available, but the 3-dimensional structure of the protein is known, site-directed mutagenesis can be used to introduce nucleotide changes giving rise to substitution of amino acids on the surface of the protein of interest in order to identify its functional sites or epitopes. However, a very large number of mutants must be constructed to completely survey the surface of the protein of interest. Further, this method of identification of functional sites or epitopes is disadvantageous in that single amino acid changes, even located close to a functional site or epitope of interest, may not have a significant effect on the activity of that functional site or epitope.

Construction of deletion mutants instead of point mutants is useful only for identification of polypeptide domains involved in protein function. Deletion of portions of a folding domain leads to generalized folding defects, making it impossible to pinpoint any amino acids involved in functional or epitopic activity (Gething, M. J. et al, *EMBO J.*, 7:2731-2740 (1988)).

Naturally occurring variants of influenza virus have been identified in which an N-linked oligosaccharide side chain apparently "shields" an antigenic epitope on the hemagglutinin glycoprotein (hereinafter "HA") that is the major surface antigen of the virion (Wiley, D. C. et al, *Nature*, 289:373-378 (1981); Caton, A. J. et al, *Cell*, 31:417-427 (1982); Raymond, F. L. et al, *Virol.*, 148:275-287 (1986); and Wiley, D. C. et al, *Ann. Review Biochem.*, 56:365-394 (1987)). This strategy for evasion of the immune system has been reproduced in the laboratory, i.e., a virus selected by growth in the presence of an anti-HA monoclonal antibody has been found to bear an altered HA that contains an additional N-linked oligosaccharide side chain which appears to be attached near to, but not within, the target antigenic epitope (Skehel, J. J. et al, *Proc. Natl. Acad. Sci. U.S.A.*, 81:1779-1783 (1984)). However, this experiment was not carried out with the intention of generating an N-linked oligosaccharide side chain-addition mutant as in the present invention.

SUMMARY OF THE INVENTION

Accordingly, an object of the present invention is to provide a simple and rapid method for identifying or shielding functional sites or epitopes of naturally occurring secretory or membrane proteins which may be available only in small quantities and without the need for the sequencing of mutants at either the gene or protein level.

Another object of the present invention is to provide a simple and rapid method for identifying or shielding functional sites of proteins which have been genetically engineered by the addition of a signal polypeptide thereto, and thus can be translocated into the secretory pathway, and which may be available only in small quantities, without the need for the sequencing of mutants at either the gene or protein level.

These and other objects of the present invention will be apparent from the detailed description of the invention provided hereinafter.

The above-described objects of the present invention have been met, in one embodiment, by a method for identifying or shielding functional sites or epitopes of a transportable protein comprising:

(1) using oligonucleotide-directed mutagenesis of selected nucleotide(s) of the gene encoding said transportable protein so as to introduce consensus sequence(s) for N-linked glycosylation in said transportable protein such that when a eukaryotic cell is transformed with the resulting gene, additional oligosaccharide side chain(s) will be attached to amino acid(s) located on the surface of said transportable protein:

(2) transforming a eukaryotic cell with the resulting gene so that said eukaryotic cell expresses said gene and glycosylates said consensus sequence(s) so as to introduce N-linked oligosaccharide side chain(s) on selected site(s) on the surface of said transportable protein; and (3) assaying for inhibition of functional or epitopic activity so as to identify or confirm the shielding of the functional sites or epitopes, respectively, of said transportable protein.

In another embodiment, the above-described objects of the present invention have been met by a mutant transportable protein having a supernumerary N-linked oligosaccharide side chain which shields a functional site or epitope: and genes which encode the same.

BRIEF DESCRIPTION OF THE DRAWINGS

FIG. 1A shows the 3-dimensional structure of the ectodomain of an HA monomer (comprising subunits HA1 and HA2) as described by Wilson, I. A. et al, *Nature*, 289:366-373 (1981). Although the HA synthesized in most tissue culture cells remains in the form of the single polypeptide HA0 precursor unless treated with exogenous protease (White, J. et al, *Nature*, 300:658-659 (1982)). it is presumed that the 3-dimensional structure shown in FIG. 1A for the post-translationally cleaved HA molecule closely represents that of the precursor except in the region close to the cleavage site (Wilson, I. A. et al, *Nature*, 289:366-373 (1981)). In FIG. 1A, the numbers refer to the position in the primary sequence of HA of the asparagine residue in the consensus sequence asparagine-X-serine/threonine (hereinafter "Asn-X-Ser/Thr"). Additional glycosylation sites which have been introduced into HA in accordance with the present invention are indicated by (+) after the number. The positions of the Asn residues of the seven natural N-linked oligosaccharide side chains are also shown.

FIG. 1B shows the nucleotide changes and corresponding amino acid changes which have been introduced into the HA monomer by oligonucleotide mutagenesis to generate the new consensus sequences for glycosylation shown in FIG. 1A. Nucleotides which have been altered by oligonucleotide mutagenesis are indicated by underlines. Mutant 54B+ was generated using mutant 54A+ DNA as a template for oligonucleotide mutagenesis. The sequences of the oligonucleotide primers used for site-directed mutagenesis are also shown.

FIG. 2 also shows the 3-dimensional structure of the ectodomain of an HA monomer as described by Wilson, I. A. et al, *Nature*, 289:366-373 (1981). The positions of the seven natural (open stars) and five additional N-linked oligosaccharide side chains (solid stars) are indicated. The positions of the four major antigenic epitopes of HA (A, B, C, D) are also shown along with a summary of the phenotypes of the five HA mutants.

FIG. 3B shows the nucleotide substitution and corresponding amino acid change in mutant t-PA67+ that introduces a supernumerary consensus sequence for glycosylation. The sequence of the oligonucleotide primer used for site-directed mutagenesis is also shown. The nucleotide (position 388, as defined by Pennica, D. et al, *Nature*, 301:214-221 (1983)) which has been altered by oligonucleotide mutagenesis is underlined.

DETAILED DESCRIPTION OF THE INVENTION

Figure 3A:
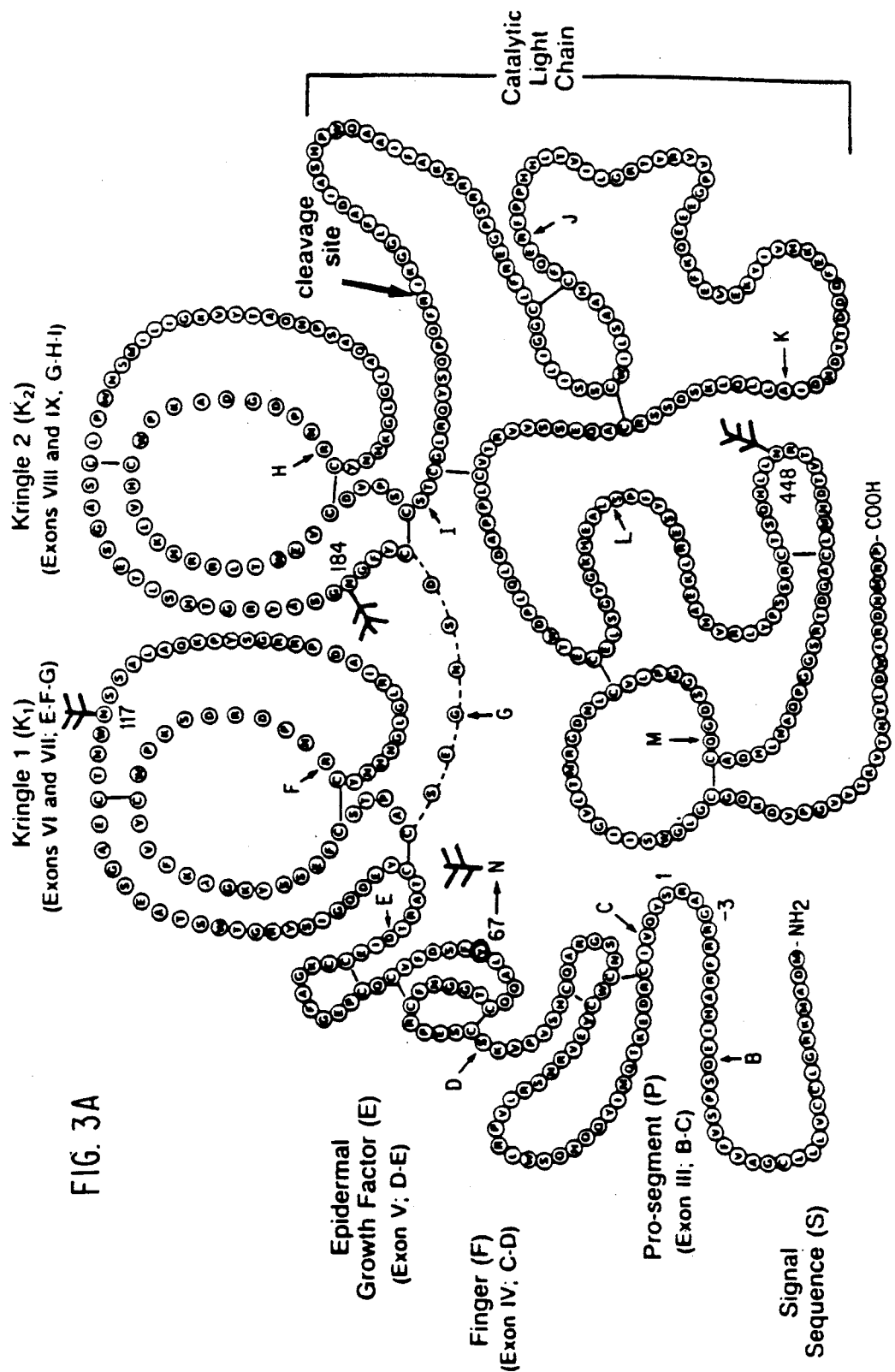
FIG. 3A shows a schematic representation of the wild-type tissue-type plasminogen activator (hereinafter "t-PA") and the mutant t-PA67+ proteins. The amino acid sequence (Pennica, D. et at, *Nature*, 301:214-221 (1983)) and the predicted secondary structure (Ny, T. et al, *Proc. Natl. Acad. Sci. U.S.A.*, 81:5355-5359 (1984)) of the precursor of t-PA is shown, including the signal sequence (S) and the pro-segment (P). The solid bars indicate the potential disulfide bridges, and the site of cleavage into heavy (H) and catalytic light (L) chains is shown by a bold arrow. The arrows marked with letters B-M indicate the map positions of individual exons in the protein (Ny, T. et al *Proc. Natl. Acad. Sci. U.S.A.*, 81:5355-5359 (1984)). The locations of the finger (F), epidermal growth factor (EGF)-like (E), and kringle 1 ($K_1$) and kringle 2 ($K_2$) domains are shown, together with notation (Roman numerals) of the exon(s) that encode each domain. The positions of the natural carbohydrate attachment sites on Asn (N) residues 117, 184 and 448 are shown, as is the position of the amino acid substitution Tyr (Y) to Asn (N) at residue 67 which introduce a novel consensus sequence for glycosylation of the EGF-like domain.

As discussed above, the above-described objects of the present invention have been met, in one embodiment, by a method for identifying or shielding functional sites or epitopes of a transportable protein comprising:

(1) using oligonucleotide-directed mutagenesis of selected nucleotide(s) of the gene encoding said transportable protein so as to introduce consensus sequence(s) for N-linked glycosylation in said transportable protein such that when a eukaryotic cell is transformed with the resulting gene, additional oligosaccharide side chain(s) will be attached to amino acid(s) located on the surface of said transportable protein;

(2) transforming a eukaryotic cell with the resulting gene so that said eukaryotic cell expresses said gene and glycosylates said consensus sequence(s) so as to introduce N-linked oligosaccharide side chain(s) on selected site(s) on the surface of said transportable protein; and (3) assaying for inhibition of functional or epitopic activity so as to identify or confirm the shielding of the functional sites or epitopes, respectively, of said transportable protein.

In another embodiment, the above-described objects of the present invention have been met by a mutant transportable protein having a supernumerary N-liked oligosaccharide side chain which shields a functional site or epitope: and genes which encode the same.

As used herein, the expression "functional site" means a small region on the surface of a protein comprising the amino acids involved in a catalytic activity or function of the protein. Such functional sites include, e.g., active sites, catalytic sites, and binding sites for ligands, such as substrates, cofactors, inhibitors or effector molecules.

As used herein, the expression "epitope" means a small region on the surface of a protein comprising the amino acids that are recognized by and/or bind to other proteins, e.g., antibodies or cellular receptors.

As used herein, the expression "transportable proteins" means secretory or membrane proteins or proteins which have been genetically engineered by the addition of a signal polypeptide thereto and thus which can be translocated into the exocytotic pathway.

The signal hypothesis (Blobel, G. et al, *J. Cell Biol.*, 67:835–851 (1975)) provides a satisfying explanation of the targeting and translocation of newly synthesized proteins across the membrane of the endoplasmic reticulum (hereinafter "ER") of eukaryotic cells. Essential to the hypothesis are the interactions between a hydrophobic segment of the secretory protein (the signal or leader) and the translocation machinery of the cell. In some circumstances, these interactions begin as the hydrophobic signal of a nascent polypeptide emerges from the ribosome and binds to a signal recognition particle (hereinafter "SRP") (Walter, P. et al, *Cell*, 38:5–8 (1984)). Synthesis of the remainder of the protein may then be halted or slowed until the bound SRP attaches to its receptor on the membrane of the ER, establishing a functional ribosome-membrane junction through which the nascent polypeptide is translocated (Walter, P. et al, *J. Cell Biol.*, 91:557–561 (1981); Walter, P. et al, *Cell*, 38:5–8 (1984); and Meyer, D., *EMBO J.*, 4:2031–2033 (1985)). In other cases, interaction between the signal sequence and the translocation machinery may not occur until synthesis of the polypeptide is completed, or nearly completed (Ainger, K. et al, *EMBO J.*, 5:951–955 (1986); Perara, E. et al, *Science*, 232:348–352 (1986); and Mueckler, M. et al, *Cell*, 44:629–637 (1986)). Although the factors that determine whether translocation is co-translational or post-translational are not well understood, it is clear that neither process occurs in the absence of a functional signal. That is, removal or mutation of the sequence coding for the signal results in proteins that cannot be translocated (Gething, M. J. et al, *Nature*, 300:598–603 (1982); Carlson, M. et al, *Cell*, 28:145–154 (1982); Chao, C. et al, *Mol. Cell Biol.*, 7:3842–3845 (1987); and Bird. P. et al, *J. Cell Biol.*, 105:2905–2914 (1987)). Conversely, addition of a signal peptide causes proteins that normally would be sequestered on the cytoplasmic side of the ER to be translocated both in vivo and in cell-free systems (Sharma, S. et al, *EMBO J.*, 4:1479–1489 (1985); Lingappa, V. et al, *Proc. Natl. Acad Sci. U.S.A.*, 81:456–460 (1984); Guan, J. L. et al, *Cell*, 37:779 (1984); and Bird, P. et al, *J. Cell Biol.*, 105:2905–2914 (1987)).

During or soon after translocation of the polypeptide into the ER, the signal sequence is cleaved off by a protease found only on the luminal side of the rough ER (Waler, P. et al, *Proc. Natl. Acad. Sci. U.S.A.*, 76:1795–1799 (1979)).

The membrane of the rough ER is impervious to cytosolic proteins. Only those proteins synthesized as precursors with signal sequences are able to pass through and reach the luminal side. Thus, segregation of secretory and surface proteins from the cytoplasmic proteins of the cell occurs at a very early stage during their synthesis and is independent of the final size and shape of the mature proteins.

Glycosylation of asparagine residues is one of the most common modifications of proteins in the exocytotic pathway and occurs in all eukaryotic cells (Olden, K. et al, *Biochim. Biophys. Acta*, 650:209–232 (1982)). As the nascent polypeptide appears on the luminal side of the rough ERm, preformed oligosaccharides composed of N-acetyl-glucosamine, mannose, and glucose (Tabas, I. et al, *J. Biol. Chem.*, 254:11655–11663 (1979)) are transferred to certain asparagine residues, i.e., those occurring in the sequences Asn-X-Ser or Asn-X-Thr (Neuberger, A. et al, In: *The Glycoproteins: Their Com-* position *Structure and Function*, Ed. A. Gottschalk, Elsevier, Amsterdam, pages 450–490 (1972)). This initial "core" glycosylation is but the first step in an elaborate program of reactions taking place both in the rough EF and later in the Golgi apparatus (Kornfeld, R. et al, *Ann. Rev. Biochem.*, 54:631–664 (1985)), wherein sugars are added to and trimmed from the nascent protein. It is also during this period that the secondary and tertiary structure of the mature protein becomes established by disulfide linkages and association between polypeptide subunits.

Proteins destined to be secreted from the cell pass completely through the membranes of the rough ER and are released into the lumen. Those that are to occupy a place on internal cell membranes, or on the surface of the cell, become anchored on the luminal surface of the membrane by one or more stretches of 20–30 hydrophobic and nonpolar amino acids. In topological terms, the lumen of the rough ER is equivalent to the outside of the cell, and its luminal surface is equivalent to the cell's outer surface. Thus, secretory proteins are released from the cell when vesicles pinched off from the Golgi apparatus fuse with the plasma membrane (Palade, G., *Science*, 189:347–358 (1975)), and integral membrane proteins become displayed on the cell surface as the lipid bilayer of transport vesicles becomes incorporated into the plasma membrane.

Examples of membrane proteins which can be employed in the present invention include enzymes such as aminopeptidases, glycosidases (e.g., sucrose-isomaltase or lactase); receptors such as low density lipoprotein receptor, transferrin receptor, asialoglycoprotein receptor, epidermal growth factor receptor, insulin receptor, T cell receptor, acetylcholine receptor, β-adrenergic receptors, cell adhesion molecules and integrins; transport proteins such as sodium channels, potassium channels, calcium channels, amino acid permeases, glucose transporters, ATP-dependent proton pumps, and anion transporters; and cell surface antigens such as Class I major histocompatibility antigens, Class II major histocompatibility antigens, other lymphocyte surface antigens, including CD8 on cytotoxic T cells and CD4 on helper T cells (the AIDS virus receptor).

Examples of secretory proteins which can be employed in the present invention include enzymes such as serine proteases (e.g., trypsin, chymotrypsin, elastase and plasminogen activators) amylases, and ribonucleases: enzyme inhibitors such as serpins (e.g., α1-antitrypsin and plasminogen activator inhibitors); cell attachment proteins such as collagen, fibronection and laminin; hormones and growth factors such as insulin, growth hormone, prolactin platelet-derived growth factor, epidermal growth factor, fibroblast growth factors, interleukins, interferons; and carrier proteins such as transferrin and albumins.

Other proteins that are not normally introduced into the exocytotic pathway can be genetically engineered so that a signal polypeptide is fused thereto. This signal polypeptide is recognized by the cell so as to translocate the resulting protein into the exocytotic pathway and glycosylate such if the protein contains a consensus glycosylation site. Examples of such other proteins which can be employed in the present invention include enzymes involved in the biosynthesis of sugars, amino acids, nucleotides, lipids and steroid hormones. Specific examples of these enzymes can be found in Stryer, L., *Biochemistry*, 3rd Ed., W. H. Freeman & Sons Co., New York, pages 315–627 (1988), which is incorporated by reference herein.

Signal polypeptides have been demonstrated on secretory and membrane proteins of all organisms studied to date (Rapoport, T. A., *CRC Crit. Rev. Biochem.*, 20:73–137 (1986)). Although there is no obvious conservation of primary amino acid sequence or length, even between signal polypeptides on proteins from the same organism, statistical analyses have suggested that signal polypeptides from both prokaryotes and eukaryotes are organized along similar lines (von Heijne, G., *Eur. J. Biochem.*, 116:419–422 (1981); and Perlman, D. et al, *J. Mol. Biol.*, 167:391–409 (1983)). A typical signal sequence appears to consist of three regions: a positively charged amino terminal (n) region, a central hydrophobic (h) region, and a more polar carboxy terminal (c) region, which defines the cleavage site (Von Heijne. G., *J. Mol. Biol.*, 184:99–105 (1985)). Of particular interest is the h region, since a number of studies have suggested that the overall hydrophobicity of a signal sequence is important to its function (Rapoport. T. A., *CRC Crit. Rev. Biochem.*, 20:73–137 (1986)). In most cases, a mutation which abolishes the function of a signal polypeptide replaces a hydrophobic residue in the h region with a charged residue (Rapoport, T. A., *CRC Crit. Rev. Biochem.*, 20:73–137 (1986)).

Because of the structural similarities between signal sequences from organisms widely separated on the evolutionary scale, it was perhaps not surprising to find that signal polypeptides from one organism can function in another. For example, the bacterial β-lactamase signal sequence is functional in vertebrate systems in vivo and in vitro (Mueller, M. et al, *J. Biol. Chem.*, 257:11860–11863 (1982); and Wiedmann, M. et al, *Nature*, 309:637–639 (1984)); the rat preproinsulin signal sequences is functional in bacteria (Talmadge, K. et al, *Proc. Natl. Acad. Sci. U.S.A.*, 77:3369–3373 (1980)); and the signal sequences of human interferon (Hitzeman, R. A. et al, *Science*, 219:620–625 (1983)) and influenza virus hemagglutinin (Jabbar, M. A. et al, *Mol. Cell. Biol.*, 7:1476–1485 (1985)) are functional in yeast. In addition, yeast invertase is translocated in mammalian systems both in vivo (Bergh, M. L. E. et al, *Proc. Natl. Acad. Sci. U.S.A.*, 84:3570–3574 (1987)), and in vitro (Perlman, D. et al, *Cell*, 25:525–536 (1981)). Further, the precursors of several other yeast proteins, such as α-factor (Julius, D. et al, *Cell*, 36:309–318 (1984)) and killer toxin (Bostian, K. A. et al, *Cell*, 32:169–180 (1983)), have been shown to translocate in mammalian in vitro systems.

Moreover, addition of a signal polypeptide can cause proteins that normally are sequestered on the cytoplasmic side of the ER to be translocated both in in vitro cell-free systems (Lingappa, V. R. et al, *Proc. Natl. Acad. Sci. U.S.A.*, 81:456–460 (1984); and Bird, P. et al, *J. Cell Biol.*, 105:2905–2914 (1987)) and in vivo (Sharma, S. et al, *EMBO J.*, 4:1479–1489 (1985)); Simon, K. et al, *J. Cell. Biol.*, 104:1165–1172 (1987); Deshaies, R. J. et al, *J. Cell. Biol.*, 105:633–645 (1987); Hiebert, S. W. et al, *J. Cell. Biol.*, 107:865–876 (1988)). In some cases the genetically-engineered hybrid protein is retained in the ER following translocation (Sharma, S. et al, *EMBO J.*, 4:1479–1489 (1985)). However, such proteins can be efficiently transported to the cell surface (Hiebert, S. W. et al, *J. Cell. Biol.*, 107:865–876 (1988)).

As discussed above, the identification of functional sites or epitopes in the present invention is broadly applicable to enzymes, receptors, hormones, etc. where it is desired to delineate the amino acids involved in an active site or binding domain. Identification of such sites or epitopes allows one to alter (increase or decrease) enzyme activity or ligand binding activity by modifying the sites by oligonucleotide-directed mutagenesis (Craik, C. S. et al, *Science*, 228:291-297 (1985); Carter, P. et al, *Nucl. Acids Res.*, 13:4431-4443 (1986); Howell, E. E. et al, In: *Protein Engineering*, Ed. Oxender, D. L. et al, A. R. Liss, Inc., New York, pages 251-256 (1987); Rutter, W. J. et al, *Ibid*, pages 257-267; Fersht, A. R. et al, *Ibid*, pages 269-278; and Wells, J. A. et al, *Ibid*, pages 279-287).

The shielding of functional sites or epitopes in the present invention is also broadly applicable to enzymes, receptors, hormones, etc. Shielding of such sites or epitopes is useful to prevent the binding of inhibitors or activators and/or to prevent binding to cellular receptors, including those involved in rapid clearance of an enzyme, hormones or other proteins from the body (Owensby, D. A. et al, *J. Biol. Chem.*, 263:10587-10594 (1988); Krause, J., *Fibrinolysis*, 2:133-142 (1988); and Schwartz, A. L. et al, *J. Biol. Chem.*, 256:8878-8881 (1981)).

Although the examples given above are all proteins synthesized in mammalian cells, the present invention is broadly applicable to transportable proteins. e.g., enzymes, receptors, hormones, etc., of other eukaryotes, including plants and unicellular organisms, including yeasts, etc.

Carrying out the present invention involves five basic elements: (1) the starting materials; (2) the selection of site(s) on the transportable protein so as to introduce consensus sequence(s) for glycosylation therein; (3) oligonucleotide mutagenesis; (4) expression of the mutant transportable protein and (5) characterization of the mutant transportable protein. Each of these elements are discussed in more detail below.

1. Starting Materials

The following starting materials are employed in order to carry out the method of the present invention: (i) a partial or full-length copy of the gene or cDNA encoding the transportable protein of interest; (ii) a single stranded DNA template containing a copy of all or part of the gene to be mutated; (iii) oligonucleotide(s) complementary to the specific site(s) to be mutagenized which are of the appropriate sequence to direct the desired base change(s); and (iv) an expression system for the production of wild-type and mutant forms of the transportable protein of interest in eukaryotic cells.

2. Selection of Sites for Introduction of Consensus Sequences

The following criteria should be used for the selection of appropriate site(s) for the introduction of consensus sequences (Asn-X-Ser/Thr) which direct the addition of N-linked oligosaccharide side chains onto transportable proteins whose 3-dimensional structure is known. These criteria are employed so as to develop minimum disruption of the global structure of the transportable protein of interest in which consensus sequences are to be introduced.

(i) The residue(s) to be altered should be exposed on the surface of the native protein.
(ii) The residue(s) to be altered should be unlikely to be important structurally, e.g., the residue(s) should not be cysteine or proline or involved in important non-covalent interactions.
(iii) When the sequences of other members of a related family of proteins are known, alteration of conserved amino acids should be avoided.
(iv) The residue designated to be the N-oligosaccharide-linked Asn should have its side chain extended away from the interior of the protein.
(v) The central residue (X) in the glycosylated consensus sequence should not be proline because Asn-Pro-Ser/Thr sequences do not specify N-linked glycosylation (Bause, E., *Biochem. J.*, 209:331-336 (1983)).

For transportable proteins whose 3-dimensional structure is not known, the above criteria should be followed where possible for the selection of sites at which consensus sequences are to be introduced. Under these circumstances, there is less certainty as to which amino acids are located on the exterior of the protein and therefore suitable for attachment of N-linked oligosaccharide side chains. However, well known algorithms (PC/Gene Analysis Programs developed by IntelliGenetics) have been designed which permit identification of stretches of charged amino acids (Hopp, T. P. et al, *Proc. Natl. Acad. Sci. U.S.A.*, 78:3824-3828 (1981); and Kyte, J. et al, *J. Mol. Biol.*, 157:105-132 (1982)) or sequences that form sharp bends in the polypeptide chain (Chou. P. Y. et al, *Adv. Enzymol.*, 47:45-148 (1978); and Garnier, J. et al, *J. Mol. Biol.*, 120:97-120 (1978)), both of which tend to be located on the outside of folded molecules. Thus, these algorithms can be employed to identify residues exposed on the surface of the native proteins.

Furthermore, a charged amino acid is more likely to have its side chain extended out from the surface of the protein. Therefore, a charged amino acid located two residues upstream of a Ser or Thr should be a good candidate for substitution by Asn.

Examination of the sequences of HAs from different virus strains indicates that where sequence variation involves the substitution of an Asn that is part of a functional glycosylation consensus sequence, this residue is variously replaced by the following hydrophilic and charged amino acids: aspartic acid, glutamic acid, histidine, lysine, glutamine, serine and threonine (Kawaoka, Y. et al, *Virol.*, 139:303-316 (1984)). These observations are consistent with the suggestion that charged amino acids, which are likely to have their side chains extended out from the surface of the protein, can be substituted by an Asn that becomes linked to an oligosaccharide, without significant disruption of the protein's structure.

3. Oligonucleotide Mutagenesis

Oligonucleotide mutagenesis is a well known procedure employed in the art and has been described in detail in Zoller, M. et al, *Meth. Enzymol.*, 100:468-500 (1983); Zoller, M. et al, *DNA*, 3:479-488 (1985); Kunkel, T., *Proc. Natl. Acad. Sci. U.S.A.*, 82:488-492 (1985); and Carter, P. et al, *Nucl. Acids. Res.*, 13:4431-4443 (1985)). The preferred procedure used in the present invention is described by Zoller, M. et al, *DNA*, 3:479-488 (1984) and involves 2-primer mutagenesis wherein a universal sequencing primer and the 5'-phosphorylated mutagenic oligonucleotide are annealed to a single stranded template DNA such as phage M13. Extension of each primer is carried out using *E. coli* DNA polymerase I (large fragment). The newly synthesized strand from the sequencing primer is ligated to the 5'-end of the mutagenic oligonucleotide by T4 DNA ligase, forming a gapped heteroduplex bearing a mismatch. Covalently-closed circular molecules are not formed since the sequencing primer is not phosphorylated. Extension and ligation are carried out for about 6–12 hours at 15° C. The DNA is diluted, then used to transform E. coli. The resulting plaques are screened for mutants by filter hybridization using the mutagenic oligonucleotide which has been radioactively-labeled as a probe. More specifically, radioactively-labeled mutagenic oligonucleotide is hybridized to a filter onto which mutant and wild-type phage DNA are bound. The principle of this procedure is that the mutagenic oligonucleotide will form a more stable duplex with a mutant clone having a perfect match than with a wild-type clone bearing a mismatch. Hybridization is carried out under conditions of low stringency where both mutant and wild-type DNA hybridize with the oligonucleotide. Upon increasing the temperature at which the filter is washed, the mutagenic oligonucleotide remains hybridized to the mutant DNA and dissociates from the wild-type DNA. At this temperature, the mutant DNA can be easily discriminated from the wild-type DNA. The temperature at which the mutant and the wild-type DNA are discriminated depends upon the particular mutation and the specific sequence of the mutagenic oligonucleotide but can be determined by routine experimentation.

Screening can be carried out by dot blot hybridization of phage DNA prepared from individually isolated plaques or by plaque hybridization where 100–200 plaques can be screened at once (Zoller, M. J. et al, *DNA*, 3:479–488 (1984)). Putative mutants are plaque-purified and single stranded DNA is prepared. DNA from the putative mutants and the wild-type control are sequenced in the region of the desired mutation using an oligonucleotide that primes approximately 60–70 bases upstream of the mutation site. Once a mutant clone is identified as having the desired sequence, the double-stranded or replicative form of the phage DNA is prepared and digested with the appropriate restriction enzymes required to isolate the mutated sequence. If only a portion of the gene has been used for mutagenesis, the restriction frequent bearing the mutated sequence is then inserted into the full-length gene, replacing the corresponding wild-type sequence.

4. Expression of the Mutant Transportable Protein

In recent years, the development of technique for the efficient introduction of DNA into cultured eukaryotic cells has led to the development of a wide variety of strategies for expressing cloned genes in a broad range of types and species of mammalian cells. Numerous reviews describe suitable vectors, host cells and procedures (Kaufman, R. J., *Genetic Engineering*, Vol. 9, Ed. Setlow, J., Plenum Press, New York (1987); and Samborrk, J. et al, *Focus*, 10:41–48 (1988)). Efficient vector-host systems have also been developed to express cloned genes in yeast (Rothstein, R., In: *DNA Cloning*, Vol. 11, Ed. Glover, D. M., IRL Press, Oxford & Washington, pages 45–66 (1986) and in plant cells (Lichtenstein, C. et al, In: *DNA Cloning*, Vol. II, Ed. Glover, D. M., IRL Press, Oxford & Washington, pages 67–119 (1986)).

The full-length gene obtained as described above can then be inserted into an appropriate expression vector and expressed in eukaryotic cells using the well known vectors and procedures employed in the art.

5. CHARACTERIZATION OF THE MUTANT TRANSPORTABLE PROTEIN

The following steps are employed to characterize the resulting mutant transportable protein.

(a) Demonstration that the introduced consensus sequence is utilized as a site for the addition of an N-linked oligosaccharide side chain Several methods are well known in the art to demonstrate that the introduced consensus sequence is utilized as a site for the addition of an N-linked oligosaccharide side chain (Sharma, S. et al, *EMBO J.*, 4:1479–1489 (1985); Guan, J. L. et al, *Cell*, 42:489–496 (1985); Hiebert, S. W. et al, *J. Cell. Biol.*, 107:865–876 (1988); and Schuy, W. et al, *EMBO J.*, 5:2831–2836 (1986)). These methods all utilize radiolabeling of cells which express the mutant transportable protein followed by immunoprecipitation of the mutant transportable protein by a specific polyclonal antibody that recognizes multiple epitopes on the protein and analysis of the resulting immunoprecipitated protein's apparent molecular weight by SDS-polyacrylamide gel electrophoresis and autoradiography.

Mutant transportable proteins that contain only a single consensus sequence for glycosylation that has been introduced by oligonucleotide mutagenesis can be determined by:

(i) a decrease in the mobility of mutant transportable proteins synthesized in cells treated with tunicamycin (an inhibitor of N-linked glycosylation) (Schwarz, R. T. et al, *Trends. Biochem. Sci.*, 5:65–67 (1980)) versus those which have been synthesized in the absence of tunicamycin (Sharma, S. et al, *EMBO J.*, 4:1479–1489 (1985); Guan, J. L. et al, *Cell*, 42:489–496 (1985); and Hiebert, S. W. et al, *J. Cell. Biol.*, 107:865–876 (1988)), (ii) incorporation of $^3$H-mannose into the mutant transportable protein but not into the wild-type protein (Sharma, S. et al, *EMBO J.*, 4:1479–1489 (1985); Guan, J. L. et al, *Cell*, 42:489–496 (1985); and Hiebert, S. W. et al, *J. Cell. Biol.*, 107:865–876 (1988)), or (iii) a decrease in mobility of the mutant transportable protein following treatment with endoglycosidase F (Hiebert, S. W. et al, *J. Cell. Biol.*, 107:865–876 (1988)).

Mutant transportable proteins that contain consensus sequence(s) for glycosylation in addition to the natural consensus sequence(s) for glycosylation found in the wild-type transportable protein can be determined by comparison of the migration on SDS-polyacrylamide gel electrophoresis of the wild-type and mutant proteins. This method allows detection of mutant proteins with decreased mobility due to the presence of an N-linked oligosaccharide side chain (Machamer, C. E. et al, *J. Biol. Chem.*, 263:5948–5954 (1988)).

Alternatively, partial digestion of N-linked oligosaccharides with endo-N-acetylglucosaminidase H (hereinafter "endo H") allows determination of the precise number of N-linked oligosaccharide side chains on the mutant transportable protein (Schuy, W. et al, *EMBO J.*, 5:2831–2836 (1986)). This method is the most direct evidence for the presence of consensus sequence(s) for glycosylation in addition to those natural consensus sequences(s) for glycosylation found in the wild-type protein.

(b) Confirmation That the Mutant Transportable Protein Reaches its Correct Final Destination Within or Outside of the Cell The choice of specific assays to determine whether or not the addition of consensus sequence(s) for glycosylation alters the normal destination of the mutant transportable protein will depend on whether it is of the membrane or secretory type.

Secretory proteins can be detected in culture supernatants of cells expressing the mutant protein by radioimmunoassay, immunoprecipitation of radiolabeled protein or activity assays (Gething, M. J. et al, *Nature*, 300:598–603 (1982); Gething, M. J. et al, In: *Genetics of Influenza Viruses*, Ed. Palese, P. et al, Springer-Verlang, Vienna, pages 169–191, (1983); and Sambrook, J. et al, *Mol. Biol. Med.,* 3:459–481 (1986)).

Membrane proteins can be detected by various assays of intact, detergent extracted or permeabilized cells. For example:

(i) indirect immunofluorescence can be used so as to identify the location of the mutant proteins within the cell or on the cell surface (Gething, M. J. et al, In: *Genetics of Influenza Viruses,* Ed. Palese, P. et al, Vienna:Springer-Verlang, pages 169–191 (1983); and Doyle, C. et al, *J. Cell. Biol.,* 100:704–714 (1985));

(ii) immunoprecipitation of mutant proteins radiolabeled in a pulse-chase protocol can be used in conjunction with digestion with endo H to characterize the extent of processing of the oligosaccharide side chains and thus to determine whether the mutant proteins are transported to the Golgi apparatus (Doyle, C. et al, *J. Cell. Biol.,* 100:704–714 (1985));

(iii) proteases can be added to the medium above the intact cells or to isolated organelles so as to ascertain the accessibility of the mutant proteins to the proteases (White, J. et al, *Nature,* 300:658–659 (1982); and Doyle, C. et al, *J. Cell. Biol.,* 103:1193–1204 (1986));

(iv) activity assays can be carried out (White, J. et al, *Nature,* 300:658–659 (1982); and Gething, M. J. et al, *J. Cell. Biol.,* 102:11–23 (1986)); and (v) binding assays of ligands specific for the mutant protein to intact cells can be carried out (Ellis, L. et al, *J. Mol. Recog.,* 1:25–31 (1988)). Examples of such ligands include radiolabeled substrates or effector molecules or, as described in Example 1, the binding of erythrocytes to HA displayed on the plasma membrane (Gething, M. J. et al, 293:620–625 (1981)).

Genetically engineered transportable proteins can be detected by similar assays (Sharma, S. et al, *EMBO J.,* 4:1479–1489 (1985); Guan, J. L. et al, *Cell,* 42:489–496 (1985); and Hiebert, S. W. et al, *J. Cell. Biol.,* 107:865–876 (1988)).

It should be noted that assays which depend upon the exposure of functional sites or epitopes (e.g., activity or binding assays) cannot be used when the relevant functional site or epitope is the one which is shielded by the supernumerary N-linked oligosaccharide side chain.

(c) Confirmation That the Mutant Transportable Protein Lacks Gross Structural Abnormalities It is not possible to assay for shielding of functional sites or epitopes unless it is possible to rule out effects of global conformational changes that might have resulted from the amino acid substitution(s) or the addition of N-linked oligosaccharide side chain(s). Procedures that can be used to monitor for correct protein folding include the use of:

(i) functional assays (Gething, M. J. et al, *Nature,* 300:598–603 (1982); Gething, M. J. et al, In: *Genetics of Influenza Viruses,* Ed. Palese, P. et al, Springer-Verlang, Vienna, pages 169–191, (1983); and Sambrook, J. et al, *Mol. Biol. Med.,* 3:459–481 (1986));

(ii) conformation-specific antibodies (Gething, M. J. et al, *Cell,* 46:939–950 (1986); and Ellis, L. et al, *J. Mol. Recog.,* 1:25–31 (1988));

(iii) commercially-available proteases to measure the sensitivity of the mutant protein thereto (Skehel, J. J. et al, *Proc. Natl. Acad. Sci. U.S.A.,* 79:968–972 (1982); Doms, D. W. et al, *J. Biol. Chem.,* 260:2973–2981 (1985); and Gething, M. J. et al, *Cell,* 46:939–950 (1986)); and (iv) quantitation of the extent of the use of additional consensus sequences for glycosylation (Guan, J. L. et al, *Cell,* 42:489–496 (1985)). Partial glycosylation at the site may indicate that all or part of the consensus sequence is normally located within the interior of the wild-type protein such that rapid folding prevents recognition by the native glycosyltransferase. Under these conditions, it is likely that addition of an N-linked oligosaccharide side chain will cause disruption of the protein structure.

(d) Determination Whether the N-linked Oligosaccharide Side Chain(s) Shields a Functional Site or Epitope As discussed above, before analyzing whether a functional site or epitope has been shielded, it is necessary to establish that the additional glycosylation site occurs with high efficiency, no gross structure abnormalities have been introduced by the addition of the N-linked oligosaccharide side chain(s) and the mutant transportable protein enters or traverses the secretory pathway.

The specific assays employed to determine whether the N-linked oligosaccharide side chain(s) shields the functional site or epitope will depend on the particular activity of the functional site or epitope. An example of such an assay is the inability of a monoclonal antibody directed against the shielded functional site or epitope to bind to the mutant protein (Skehel, J. J. et al, *Proc. Natl. Acad. Sci. U.S.A.,* 81:1779–1783 (1984)). Synthesis of the mutant glycoprotein in cells which have been treated with tunicamycin should restore binding of the antibody. Assays that measure the binding of specific molecules or substrates which may be blocked by N-linked oligosaccharide side chain(s) or the inhibition of enzymatic activities as a result of the N-linked oligosaccharide side chain(s) can also be employed (Gething, M. J. et al, *Nature,* 300:598–603 (1982); Gething, M. J. et al, In: *Genetics of Influenza Viruses,* Ed. Palese, P. et al, Springer-Verlang, Vienna, pages 169–191, (1983); Sambrook, J. et al, *Mol. Biol. Med.,* 3:459–481 (1986); and Ellis, L. et al, *J. Mol. Recog.,* 1:25–31 (1988)).

The method of the present invention has the following advantages over current approaches for identifying and locating functional sites or epitopes:

(i) Introduction of a point mutation that leads to the addition of an N-linked oligosaccharide side chain(s) rather than one that causes only a single amino acid change increases the area of the protein which can be assayed. That is, although some single amino acid substitutions prevent folding or cause long-range disruption of protein structure, in the majority of mutant proteins, structural changes are confined to the immediate vicinity of the amino acid substitution (Knossow, M. et al, *Nature*, 311:678–680 (1984); and Matthews, B. W., In: *Protein Engineering*, Ed. Oxender, D. L. et al, A. R. Liss, Inc., New York, pages 225–226 (1987)). On the other hand, an N-linked oligosaccharide side chain can shield an average area covering a number of amino acids. Thus, the number of point mutations that are needed to be constructed to probe the protein surface in search for a functional site or epitope is too large for the approach to be feasible in the absence of a genetic screen. However, many fewer N-linked oligosaccharide side chain-addition mutants are sufficient to survey the entire surface of a protein. Once the general location of a functional site or epitope has been identified using the method of the present invention, specific mutagenesis of amino acids in this area can be used, if desired, to dissect the features of the functional site or epitope.

(ii) Shielding by N-linked oligosaccharide side chains is more likely to have an all or none effect on the protein function as compared to alteration of a single amino acid. That is, as discussed in more detail below, while the addition of an N-linked oligosaccharide to $Asn_{188}$ in HA completely abolishes sialic acid binding, substitutions of a number of residues located within the receptor pocket either have no effect or change only the specificity or affinity of binding (Wiley, D. C. et al, *Ann. Review Biochem.*, 56:365–394 (1987); and Daniels, R. S. et al, *EMBO J.*, 6:1459–1465 (1987)).

(iii) In those cases where the natural N-linked oligosaccharide side chains are not required for correct folding and transport (Elbein, A. D., *Ann. Rev. Biochem.*, 56:497–534 (1987)) it is possible after using the method of the present invention, to test directly whether abolition of function results from shielding of the functional site or epitope. That is, synthesis of the non-glycosylated polypeptide in the presence of tunicamycin allows dissection of any contribution of the amino acid substitution itself to the altered phenotype of the mutant transportable protein.

(iv) Using the method of the present invention, addition of N-linked oligosaccharide side chain(s) occurs as a natural consequence of entry into the ER. That is, the additional N-linked oligosaccharide side chain(s) are processed during transport along the exocytotic pathway in the same manner as natural N-linked oligosaccharide side chains on glycoproteins in the same cell so that its final structure will not be recognized as foreign by elements of the immune system. Further, the addition of N-linked oligosaccharide side chain(s) should shield from the immune system any amino acids that have been altered to form the consensus sequence (Asn-X-Ser/Thr) for glycosylation. Thus, mutant transportable proteins produced in this manner are less likely to induce an immune response than other proteins that have been altered by genetic engineering, a feature of importance if a protein engineered in this manner is to be administered as a drug.

(v) The technique of oligonucleotide mutagenesis employed in the method of the present invention to introduce consensus sequences for glycosylation, is a simple, widely practiced technique.

The following examples are provided for illustrative purposes only and are in no way intended to limit the scope of the present invention.

EXAMPLE 1

In this example, a series of mutant HA proteins, each containing a new consensus sequence for glycosylation, in addition to the seven natural consensus sequences found on the wild-type protein, have been constructed in order to identify and shield the functional sites and epitopes on the surface of HA. However, the procedures described in detail below can be readily employed with other transportable proteins so as to identify and shield the functional sites or epitopes thereof.

The biosynthesis, processing and intracellular transport of HA has been analyzed in great detail (Compans, R. W. et al, In: *Comparative Virology*, Ed. Maramorosch, K. et al, Academic Press, New York, pages 407–432 (1971); Elder, K. T. et al, *Virol.*, 95:343 (1979); Rodriguez-Boulan, E., In: *Modern Cell Biology*, Ed. Satir, B., A. R. Liss, Inc., New York, pages 119–170 (1983); Matlin, K. et al, *J. Cell Biol.*, 99:2131 (1984); and Gething, M. L. et al, *Cell*, 46:939–950 (1986)). The resolution of the 3-dimensional structure of the ectodomain of HA from the A/Aichi/68(X-31) strain of influenza virus hereinafter "X-31 HA") (Wilson, I. A. et al, *Nature*, 289:366–373 (1981)) has demonstrated that the mature protein is a trimer of identical subunits each of which is comprised of two major structural domains, i.e., HA1-a globular "head" which contains four major antigenic epitopes as well as the receptor for sialic acid (Wilson, I. A. et al, *Nature*, 289:366–373 (1981)), and HA2-a fibrous-α-helical "stem", 76 Å in length, which contains one or more hydrophobic sequences involved in the membrane fusion activity of the HA molecule (Gething, M. J. et al, *J. Cell Biol.*, 102:11–23 (1986)). As discussed above, seven N-linked oligosaccharide side chains are naturally attached to each subunit of the X-31 HA molecule (Wilson, I. A. et al, *Nature*, 289:366–373 (1981)). These N-linked oligosaccharide side chains are all bound to Asn residues that are located on the surface of both the "head" and "stem" portions of the protein (Wiley, D. C., *Nature*, 289:373–378 (1981)) (see FIG. 1A).

HAs comprise a large family of highly polymorphic glycoproteins which may vary up to 60% in amino acid sequence while still retaining very similar structure and biological properties (Wilson, I. A. et al, *Nature*, 289:366–373 (1981); and Wiley, D. C. et al, *Nature*, 289:373–378 (1981)). This extensive sequence variation, which allows newly evolved viruses to escape immunity acquired by the host during previous infection, may either occur gradually by the accumulation of single amino acid changes (antigenic drift), or abruptly after the introduction of a novel HA gene from an animal reservoir (antigenic shift) (Air, G. M. et al, *Contrib. Microbiol. Immunol.*, 8:22–59 (1987)). There is also considerable variation in the position and number (four to nine) of potential carbohydrate attachment sites on the different HA molecules (Klenk, H. D., In: *Structure and Variation in Influenza Virus*, Ed. Laver, G. et al, Elsevier Science Publishing Co., Inc., New York, pages 213–222 (1980); Wilson, I. A. et al, *Biochem. Soc. Trans.*, 11:145–147 (1983); and Keil, W. H. et al, *Virol.*, 133:77–91 (1984)). Occasionally, when antigenic shift or drift creates a novel consensus sequence (Asn-X-Ser or Thr) for N-linked glycosylation, the addition of the new N-linked oligosaccharide side chain may modulate the immune recognition of the molecule by shielding an antigenic epitope (Wiley, D. C. et al, *Nature*, 289:373-378 (1981); Caton, A. J. et al, *Cell*, 31:417-427 (1982); and Raymond, F. L. et al, *Virol.*, 148:275-287 (1986)). Because evasion of the immune system appears to be the major evolutionary pressure on influenza virus, it might be expected that, with time N-linked oligosaccharide side chains would progressively cover more of the surface of the HA molecule. However, comparison of the glycosylation sites on a large number of HA variants reveals that although a majority of the protein's surface has been shielded by an N-linked oligosaccharide side chain at one time or another during the evolution of the protein, five specific surface areas appear always to have lacked an N-linked oligosaccharide. In only one case is there an obvious reason for the absence of an oligosaccharide. At the apex of the protein, near the contact points between the globular domains of the three subunits, there is a sialic acid binding site involved in the attachment of the virus to host cells (Wilson, I. A. et al, *Nature*, 289:366-373 (1981)). N-linked oligosaccharide side chains shielding this region would mask the binding site and abolish its activity. Other regions of HA which must remain devoid of N-linked oligosaccharides might include recognition site(s) for putative cellular transport proteins involved in either the initial folding and mobilization of HA into the secretory pathway (Gething, M. J. et al, *Cell* 46:939-950 (1986)), and-/or the directional transport of HA to the apical surface of polarized epithelial cells (Fitting, T. et al, *J. Biol. Chem.*, 257:14011-14017 (1982); Rodriguez-Boulan, E. et al, *Cell*, 20:45-55 (1978); and Blobel, G., *Proc. Natl. Acad. Sci. U.S.A.*, 77:1496-1500 (1980)). Alternatively, exclusion of N-linked oligosaccharide side chains from surface areas might occur for structural reasons. That is, attachment of the N-linked oligosaccharide side chains at some positions could interfere either with correct folding and oligomerization of the molecule (Gething, M. J. et al, *Cell*, 46:939-950 (1986)) or with assembly of influenza virus into infectious virions.

In order to analyze these and other possibilities, oligonucleotide mutagenesis has been employed in the present invention so as to introduce consensus sequences for N-linked oligosaccharide side chains into a cloned copy of the gene encoding X-31 HA. This example describes the characterization of five mutant HAs, each of which has a novel consensus sequence located within one of the five barren regions discussed above on the surface of HA. Further, this example demonstrates that the addition of N-linked oligosaccharide side chains can be used to shield functional sites and epitopes on the surface of the HA molecule.

A. Selection of Sites for Introduction of Consensus Sequence

The 3-dimensional structure of X-31 HA (Wilson, I. A. et al, *Nature*, 289:366-373 (1981)) was displayed on an Evans and Sutherland color multi-picture system. Analysis of the protein structure was performed using a Digital Electronics Company VAX11/750. The structure representations were projected using GRAMPS (O'Donnell, T. J. et al, *Comput. Graphics*, 15:133-142 (1981)) and GRANNY (Connolly, M. L. et al, *Comput. and Chem.*, 9:1-6 (1985)) programs. The HA1 amino acid sequences reported for the 47 HA variants and the HA2 amino acid sequences reported for the 22 HA variants were collated and the positions of all of the natural glycosylation sites on the HA proteins were noted. The positions of all of the residues that have, in one sequence or another, been Asn of a consensus glycosylation sequence were amassed on the X-31 HA structure. These glycosylation sites can be grouped into three classes, i.e., those whose position is conserved in all HAs, those whose general location on the HA surface remains relatively constant although the specific point of oligosaccharide linkage to the protein may vary, and those which specify attachment of an oligosaccharide at quite different positions on different HAs. The projected surface area that would be "shielded" by the N-linked oligosaccharide side chains was estimated, highlighted and displayed by molecular graphics. Five barren areas of the surface of the HA trimer that appeared never to have been shielded by N-linked oligosaccharides were noted and approximate locations were selected for the attachment of novel N-linked oligosaccharide side chains that would cover these areas. Precise selection of residues to be altered to yield new consensus sequences using the criteria described above, was made utilizing a solid 3-dimensional molecular model based on the coordinates determined by X-ray crystallography (Wilson, I. A. et al, *Nature*, 289:366-373 (1981)).

FIGS. 1A and 1B show the positions on X-31 HA that were chosen for attachment of additional N-linked oligosaccharide side chains and the amino acid changes that were introduced by oligonucleotide mutagenesis to create the novel consensus sequences. Within two of the barren areas, at residues 54 and 188, a suitable Asn was available whose side chain was directed outward. Thus, a consensus sequence could be introduced by substituting a Thr or Ser residue for the amino acid located two residues further along the polypeptide chain. Because the presence of a Pro residue at the X position of the consensus sequence has been reported to prevent glycosylation (Bause, E., *Biochem. J.*, 209:331-336 (1983)), a secondary mutant was constructed in which $Pro_{55}$ was substituted by a Gly residue i.e., the amino acid which is present in this position in the majority of HAs whose sequence is known. In two other barren areas, Thr or Ser residues lay two amino acids downstream of residues (46 and 225) that were suitable for substitution by Asn. In the final barren region, both the Asn (at position 476) and the Thr residue had to be introduced by oligonucleotide mutagenesis.

B. Oligonucleotide Mutagenesis

A full length cDNA copy of the virion RNA encoding the X-31 HA gene from influenza virus strain A/Aichi/68 (Doyle, C. et al, *J. Cell Biol.*, 103:1193-1204 (1986)) was constructed as described in Doms, R. W. et al, *J. Virol.*, 60:833-339 (1986)).

More specifically, 5.0 mg of purified X-31 HA virus dissolved in 300 $\mu$l of PBS was disrupted on ice in 2.0 ml of lysis buffer comprising 10 mM Tris-HCl (pH 8.6), 140 mM NaCl, 1.5 mM $MgCl_2$, 0.5% (v/v) Nonidet P-40, and 0.015% (w/v) Macaloid (American Baroid Corp.). Virion proteins were then digested for 45 minutes at 37° C. with proteinase K after the addition of 2.0 ml of a solution comprising 200 mM Tris-HCl (pH 7.5), 300 mM NaCl, 25 mM EDTA, 2.0% (w/v) SDS, and 1.0 mg of proteinase K. The reaction mixture was then extracted twice with phenol and once with chloroform and precipitated twice with ethanol. The yield of purified viral RNA was approximately 50 $\mu$g.

First-strand cDNA synthesis from 7.0 μg of viral RNA template was performed essentially as described by Maniatis, T. et al, *Molecular Cloning*, Cold Spring Harbor (1982) except that a specific oligonucleotide primer complementary to the 3' terminus of influenza RNAs (dAGCAAAAGCAGG), replaced the oligo(dT) primer, and treatment with methylmercuric hydroxide was omitted.

Second-strand cDNA synthesis was carried out with reverse transcriptase as described by Maniatis, T. et al, *Molecular Cloning*, Cold Spring Harbor (1982).

The resulting double stranded cDNA was then ligated with phosphorylated ClaI linkers as described by Maniatis, T. et al, *Molecular Cloning*, Cold Spring Harbor (1982) so as to attach the linkers to the end of the DNA corresponding to the 3' terminus of the original virus RNA. Then, the reaction mixture was diluted so that the composition of the buffer was 10 mM Tris-HCl (pH 7.5), 60 mM NaCl and 6.0 mM $MgCl_2$ and heated to 70° C. for 10 minutes to inactivate the ligase enzyme. Next, the ligated DNA was digested with 60 Units of ClaI for 5 hours at 37° C. to generate a single ClaI sticky end on each cDNA.

It has been shown by Verhoeyen, M. et al, *Nature*, 286:771–776 (1980) that the X-31 HA gene sequence contains a single BamHI restriction site at nucleotide 1618, a position that corresponds in the amino acid sequence to the junction between the external ectodomain and the transmembrane region. Thus, the cDNA was digested with 20 Units of BamHI to generate a ClaI-BamHI fragment of HA cDNA of approximately 1600 base pairs. The digested cDNA mixture was chromatographed on a 1.0 ml column of Sepharose CL-4B in 10 mM Tris-HCl (pH 7.5), 300 mM NaCl and 1.0 mM EDTA. 150 μl fractions were collected and portions of these fractions were separated by electrophoresis on a 6.0% (w/v) polyacrylamide gel. The fractions containing cDNAs longer than 1000 base pairs were pooled and concentrated by ethanol precipitation before ligation to plasmid pXf3 (Maniatis, T. et al, *Molecular Cloning*, Cold Spring Harbor (1982)) which had previously been digested with ClaI and BamHI. *E. coli* DH-1 cells were then transformed with the mixture of ligated plasmids. Bacterial colonies containing X-31 HA sequences were identified by hybridization with a fragments from a partial cDNA clone of wild-type X-31 HA cDNA (Gething, M. J. et al, *Nature*, 287:301–306 (1980)) labelled with $^{32}P$ by nick translation as described by Maniatis, T. et al, *Molecular Cloning*, Cold Spring Harbor (1982). Plasmid DNAs were prepared from individual colonies, and clones containing the appropriate sized ClaI-BamHI fragment were identified by restriction digestion. The identity of plasmids containing the X-31 HA gene sequences was confirmed by more extensive endonuclease digestion with reference to the known restriction map (Verhoeyen, M. et al, *Nature*, 286:771–776 (1980)), and the HA gene sequences were purified and cloned into M13 vectors (Sanger, F. et al, *Mol. Cell Biol.*, 143:161–178 (1980)) for dideoxy sequencing analysis by the chain termination technique (Sanger, F. et al, *Proc. Natl. Acad. Sci. U.S.A.*, 74:5436–5467 (1977)) with either the M13 universal primer or oligonucleotides complementary to sequences spaced along the X-31 HA cDNA.

Cloning of the remaining nucleotides, corresponding to the transmembrane domain and cytoplasmic sequences of the wild-type X-31 HA gene involved primer extension using a 316 base pair XhoI-BamHI restriction fragment (nucleotides 1302–1618) isolated from the 3' terminus of the partial cDNA clone. This fragment was annealed to total Aichi virion RNAs and double-stranded cDNA synthesis was carried out as described by Maniatis, T. et al, *Molecular Cloning*, Cold Spring Harbor (1982). After second strand synthesis, the 3' terminus hairpin loop was excised using S1 nuclease and the DNA ends were repaired using the Klenow fragment of DNA polymerase I before ligation to phosphorylated SalI linkers. The double-stranded DNA molecules were then cleaved with BamHI and SalI to yield fragments of about 110 base pairs which were inserted into the M13 cloning vector, mp18 (Messing, J. et al, *Gene*, 19:269–276 (1982); and Sanger, F. et al, *J. Mol. Biol.*, 143:161–178 (1980)). Single-stranded DNAs were prepared from single plaque isolates and clone mp18-HA-TMT containing the complete carboxy-terminal coding region was identified by DNA sequence analysis using the chain termination technique (Sanger, F. et al, *Proc. Natl. Acad. Sci. U.S.A.*, 74:5436–5467 (1977)). The double-stranded replicative form of the M13 DNA was prepared from phage containing this complete sequence. The 112 base pair BamHI-SalI fragment encoding the transmembrane and cytoplasmic domains of X-31 HA was isolated and inserted into an SV40 vector as described below downstream of the sequences encoding the X-31 HA ectodomain to generate a full length cDNA copy of the HA gene.

Vector SVEXHA-A⁻ was constructed to express the X-31 HA ectodomain. This vector closely resembles SVEHA20-A⁻ which has been used to express the ectodomain of the HA gene from the A/Japan/305/57 strain of influenza virus (Gething, M. J. et al, *Nature*, 300:598–603 (1982)). Vector SVEXHA-A⁻ contains the ClaI-BamHI restriction fragment encoding the X-31 HA ectodomain inserted between the HpaII (nucleotide 346) and BamHI (nucleotide 2533) restriction sites of SV40 DNA, so that the HA sequences replace the late region of the SV40 genome which encodes the capsid proteins. For amplification and manipulation of the DNA sequences, the SV40 genome was inserted through the unique KpnI site in the SV40 sequence into plasmid pKSB (Doyle, C. et al, *J. Cell Biol.* 100:704–714 (1985)).

To construct a vector that contains the full length copy of the wild-type X-31 HA gene, vector SVEXHA-A⁻ was cleaved with BamHI and a BamHI-SalI-XhoII adaptor linker was inserted into the BamHI site. The 112 base pair BamHI-SalI fragment encoding the carboxy-terminal sequences of HA was then inserted between the new BamHI and SalI sites of the vector to yield pSVEXHA.

Then, pSVEXHA, which contains the full length cDNA copy of the X-31 HA gene from influenza virus strain A/Aichi/68, was digested with PstI and BamHI restriction endonucleases. A resulting 2579 base pair DNA fragment, including 771 base pairs of pBR322 sequences that lie between the PstI and ClaI restriction sites, and 1608 base pairs encoding the ectodomain of X-31 HA, was then purified by 5.0% (w/v) polyacrylamide gel electrophoresis as described in (Maniatis, T. et al, *Molecular Cloning*, Cold Spring Harbor (1982). This fragment was inserted between the PstI and BamHI site of the double-stranded replicative form of M13mp19 phage DNA (New England Biolabs, Beverly, Mass.), and *E. coli* TG1 cells were transfected with the ligated DNA molecules as described in Hanahan, D, *J. Mol. Biol.*, 166:557–580 (1983). Plaque hybridization (Zoller, M. et al, *DNA*, 3:479–488 (1984)), using the 1608 base pair ClaI-BamHI fragment of X-31 HA cDNA labelled with $^{32}P$ by nick translation as described above, was used to identify a recombinant phage in which the single-stranded DNA purified from M13mp19 virions secreted from infected *E. coli* TG1 contained the coding sequences of the X-31 HA cDNA.

Next, six 20-mer oligonucleotides were synthesized to be complementary, except for the required mismatches, to the X-31 HA cDNA sequences encoding regions of the protein where amino acid substitutions were planned to introduce novel Asn, Ser or Thr residues (see FIG. 1B). The procedures used to carry out oligonucleotide mutagenesis and identification of the desired mutants are well known in the art and are described in detail in Zoller, M. et al, *Methods Enzymol.*, 100:468–500 (1983); Zoller, M. et al, *DNA*, 3:479–488 (1984); and Doyle, C. et al, *J. Cell Biol.*, 103:1193–1204 (1986).

Once the desired base substitutions had been confirmed, the double-stranded replicative form of the recombinant phage DNAs containing each mutant X-31 HA sequence was prepared and purified by centrifugation on a CsCl-Ethidium bromide isopycnic gradient as described by Zoller, M. et al, *DNA*, 3:479–488 (1984) and digested with ClaI and BamHI restriction endonucleases.

The 1608 base pair ClaI to BamHI DNA fragments from the recombinant phage DNAs, which encode the X-31 HA ectodomains, and the approximately 7000 base pair BamHI-ClaI fragment of pSVEXHA, which contains nucleotides 2533–5243 and 1–346 of SV40 DNA interrupted at the KpnI site at nucleotide 294 by the sequences of pKSB (Doyle, C. et al, *J. Cell. Biol.*, 100:704–714 (1985)) were prepared by restriction endonuclease digestion and purified by electrophoresis on 5.0% (w/v) polyacrylamide gels as described by Maniatis, T. et al, *Molecular Cloning*, Cold Spring Harbor (1982).

Each of the purified fragments encoding mutant X-31 HA ectodomains were ligated to the fragment containing SV40 and plasmid sequences using T4 DNA ligase and the ligated DNAs were transfected into *E. coli* DH-1 cells as described in Hanahan, D., *J. Mol. Biol.*, 166:557–580 (1983) so as to generate SV40-HA recombinant vectors in which the wild-type X-31 HA gene was replaced by the various mutant HA genes.

Before generation of recombinant virus stocks, the pKSB sequences were removed by digestion with KpnI, and the recombinant SV40-HA genome was purified by gel electrophoresis on 5.0% (w/v) polyacrylamide gels and recircularized by dilute (less than 3.0 μg/ml) ligation to generate closed-circular SV40-HA genomes as described by Maniatis, T. et al, *Molecular Cloning*, Cold Spring Harbor (1982).

In the above manner, SV40-HA recombinant genomes were constructed in which either the wild-type X-31 HA gene or the mutant genes (46+, 54A+, 54B+, 188+, 225+, and 476+) replaced the coding sequences of the late region of SV40 DNA. The SV40-HA recombinant genomes containing wild-type DNA and mutant forms of the X-31 HA gene were transfected into CV-1 cells using DEAE-dextran and chloroquine as described in Doyle, C. et al, *J. Cell Biol.*, 100:704–714 (1985). High titer virus stocks were prepared and used to infect fresh monolayers of CV-1 cells for analysis of the biosynthesis, intracellular transport, structural conformation and phenotype of wild-type and mutant X-31 HAs as described in detail below. The conditions for growth and infection of the CV-1 cells were as described in Doyle, C. et al, *J. Cell Biol.*, 100:704–714 (1985).

C. Analysis of the Biosynthesis, Intracellular Transport, Structural Conformation and Phenotype of Wild-type and Mutant HAs (1) Analysis of the Number of N-linked Oligosaccharide Side Chains on the Wild-type and Mutant X-31 HAs To determine whether the introduced consensus sequences were recognized as additional sites for N-linked glycosylation of the nascent polypeptide chain, the mobility in SDS-polyacrylamide gel electrophoresis, of the core-glycosylated precursor form (HAO) form of each of the mutant HAs was compared with that of the wild-type X-31 HA (Gething, M. J., et al *Cell* 46:939–950 (1986)).

More specifically, about $10^6$ CV-1 cells infected for 40 hours at 37° C. with 3.0 to $5.0 \times 10^7$ p.f.u. of the SV40-HA recombinant viruses were labeled with 100 μCi per 250 μl of $^{35}S$-methionine (specific activity: 800 Ci/mmole) in the absence or presence of 5.0 μg/ml of tunicamycin in Dulbecco's modified Eagles medium (hereinafter "DMEM") lacking methionine for 5 minutes. When tunicamycin was employed, cells were treated with tunicamycin 2 hours prior to labeling and throughout the labeling procedure. The infected CV-1 cells were then washed once with a solution comprising 25 mM Tris-HCl (pH 7.4) and 140 mM NaCl, and cell extracts were prepared as described in Gething, M. J. et al, *Cell* 46:939–950 (1986) by the addition of 1.0 ml of ice-cold lysis buffer comprising 50 mM Tris-HCl (pH 8.0), 150 mM NaCl and 1.0% (v/v) Nonidet P-40. The lysed cells were scraped into a microfuge tube, vortexed for 15 seconds and centrifuged for 1 minute at $12,000 \times g$ to pellet nuclei and cell debris, and the supernatant extract collected into a fresh tube.

Next, proteins were immunoprecipitated from the cell extracts with a polyclonal anti-X31 HA rabbit antiserum as described in Gething, M. J. et al, *Cell,* 46:939–950 (1986), or with monoclonal antibodies as described in Webster, R. G. et al, *Virol.,* 126:587–599 (1983); and Gething, M. J. et al, *Cell,* 46:939–950 (1986).

The monoclonal antibodies used were 11/4 (A site), 17/2 (B site), 69/1 (C site) and 78/6 (D site) (see FIG. 2). These monoclonal antibodies were characterized as to their epitopic specificity and provided by R. Webster of St. Jude Childrens Research Hospital, Memphis, Tenn.

Thereafter, the immunoprecipitated proteins were subjected to electrophoresis on 10% (w/v) SDS-polyacrylamide gels (Laemmli, U.K., *Nature,* 227:680–685 (1970) and autoradiographed (Hahn, E. J., *American Laboratory,* July 1983).

The autoradiography showed that HA mutants 46+, 54B+, 198+ and 476+ migrated more slowly than the wild-type HA. with an increase in apparent molecular weight that is consistent with the presence of one additional N-linked oligosaccharide side chain. Non-glycosylated forms of the wild-type and mutant HAs synthesized in the presence of tunicamycin migrated with identical apparent molecular weights. Thus, the differences in mobility of the HAO species reflects changes in the complement of N-linked oligosaccharide side chains rather than in alterations in the polypeptide backbone.

The mobility differences that reveal the presence of additional N-linked oligosaccharide side chains for the HA mutants were more apparent following cleavage of the X-31 HA precursor, in DMEM containing 5.0 μg/ml of trypsin for 15 minutes before the cell extracts were prepared, into its X-31 HA1 and X-31 HA2 subunits. In addition, using this method, it was possible to assign the additional N-linked oligosaccharide side chains to the X-31 HA1 or X-31 HA2 subunit. As expected, mutants 46+, 54B+ and 198+ increased the mobilities of the X-31 HA1 subunit, while the mobility of the X-31 HA2 subunit was increased with mutant 476+.

The glycosylated forms of mutants 54A+ and 225+ migrated with the same mobility as wild-type X-31 HA. This suggests that the new consensus sequences were not utilized for glycosylation. As discussed above, it is likely that the sharp turn in the polypeptide chain caused by the Pro residue prevents the necessary simultaneous recognition of the Asn and Thr residues by the glycosyltransferase (Bause, E., Biochem. J., 209:331–336 (1983)) since substitution of a Gly residue for the Pro residue results in supernumerary glycosylation of the 54B+ mutant.

The structural basis for the lack of the novel glycosylation site in the 225+ mutant is less easily understood. Inspection using molecular graphics of the positions of the amino acids in the vicinity of residue 225 in the final conformation of the wild-type protein revealed that the aromatic ring of $Trp_{222}$ lies 4.9 Å above the $C_\alpha$ atom of $Gly_{225}$. Since the conformation of the mutant protein is not known at the time of glycosylation, it is difficult to judge whether this bulky residue could sterically hinder the access of the glycosyltransferase to the introduced Asn residue in mutant 225+.

Accurate analysis of the number of N-linked oligosaccharide side chains on each HA mutant was carried out by partial digestion with endo H (ICN Immunobiologicals, Irvine, Calif.) as described in Schuy, W. et al, EMBO J., 5:2832–2836 (1986).

More specifically, X-31 HA mutants extracted from about $10^5$ infected CV-1 cells labelled for 5 minutes at 37° C. with $^{35}$S-methionine were immunoprecipitated with polyclonal anti-X-31 serum and then digested with 4.0 mIU of endo H in 260 μl of buffer comprising 0.1M Tris-HCl (pH 8.0), 1.0% (w/v) SDS and 1.0% (v/v) β-mercaptoethanol at intervals for between 30 sec and 3 hours. At each time point, a 20 μl aliquot was removed and added to an equal volume of gel sample buffer comprising 20 mM Tris-HCl (pH 6.8), 2.0% (w/v) SDS, 15% (v/v) glycerol and 0.1 mM DTT. The samples were then analyzed by 10% (w/v) SDS-polyacrylamide gel electrophoresis and autoradiographed as described in Schuy, W. et al, EMBO J., 5:2831–2836 (1986).

At each time point, a series of discrete bands were seen in the autoradiographs, each differing by one N-linked oligosaccharide side chain. The total number of N-linked oligosaccharide side chains on the wild-type or mutant X-31 HAs were calculated from the total number of bands. Using this analysis, the previous report of seven N-linked oligosaccharide side chains on the wild-type X-31 HA (Nakamura, K. et al, Virol., 95:8–23 (1979) and Wilson, I. A. et al, Nature, 289:366–373 (1981)) was confirmed. Further, using this analysis it was seen that mutants 46+, 54B+, 198+ and 476+ each contained eight N-linked oligosaccharide side chains. Thus, this analysis verifies that the additional consensus sequence in each of these mutant HAs was utilized efficiently. As expected from the initial analysis, mutants 54A+ and 225+ contained only seven N-linked oligosaccharide side chains.

(2) Analysis of the Intracellular Transport and Processing of the Wild-type and Mutant HAs In a standard pulse-chase protocol, acquisition by a glycoprotein of resistance to cleavage of its N-linked oligosaccharide side chains by endo H provides a convenient measure of the transit time from the ER to the medial Golgi cisterna (Kornfeld, R., Ann. Rev. Biochem., 54:631–664 (1985)).

Using the procedures described in Owen, M. J. et al, J. Biol. Chem., 255:9678–9684 (1980), the mutant HAs were found to display extensive variation in their rate of acquisition of resistance to endo H after synthesis at 37° C. Densitometric analysis of the autoradiographs from these experiments allowed quantitation of the percentage of HA molecules that had become resistant to endo H at the different times after synthesis. The results are shown in Table I below.

TABLE I

Results of the Quantitation by Densitometry of the Time Course of Acquisition of Wild-type and Mutant X-31 HA Proteins of Resistance to Endo H

| | % HA molecules resistant to endo H | | |
|---|---|---|---|
| | 15 minute pulse | +15 minute chase | +2 hour chase |
| X-31 HA | 0 | 25 | 80 |
| X-31 HA46+ | 0 | 23 | 83 |
| X-31 HA54A+ | 0 | 16 | 54 |
| X-31 HA54B+ | 0 | 14 | 59 |
| X-31 HA188+ | 0 | 12 | 77 |
| X-31 HA255+ | 0 | 30 | 76 |
| X-31 HA476+ | 0 | 3 | 7 |

The accuracy of the densitometry measurements was ±3% in repeated analyses.

As shown in Table I above, two mutants, i.e., 46+ and 225+, were processed at rates very similar to that of the wild-type protein. Mutants 54A+, 54B+, and 188+ were processed more slowly and mutant 476+ showed very little conversion (about 7% during a 2 hour chase period) to a form resistant to endo H. This suggests that the majority of molecules of mutant 476+ are restricted to the ER.

The time course of appearance of newly synthesized protein on the plasma membrane was assayed by analyzing its accessibility to proteolysis by trypsin added to the external medium as described by Doyle, C. J. et al, J. Cell Biol., 103:1193–1204 (1986). Previous experiments have shown that greater than 90% of the radiolabeled, wild-type X-31 HA protein becomes accessible to exogenously added trypsin with 2 hours of chase (Doyle, C. J. et al, J. Cell Biol., 103:1193–1204 (1986)).

Accordingly, approximately $10^5$ CV-1 cells were infected with 3 to $5 \times 10^7$ p.f.u. of the SV40-HA recombinant viruses and pulse-labeled with 100 μCi per 250 μl of $^{35}$S-methionine (specific activity: 800 Ci/mmole) for 5 minutes at 37° C. and for 2 hours in serum-free DMEM containing an excess (2.0 mM) of non-radioactive methionine. For the last 15 minutes of the chase period, trypsin was added at a concentration of 5.0 μg/ml sufficient to cleave any X-31 HA on the plasma membrane into its component HA1 and HA2 subunits (White, J. et al, Nature, 300:658–659 (1982); and Doyle C. et al, J. Cell Biol., 103:1193–1204 (1986)). The radiolabeled X-31 HAs were immunoprecipitated from cell extracts using anti-HA polyclonal serum and subjected to 10% (w/v) SDS-polyacrylamide gel electrophoresis as described above.

The results of the analysis of the wild-type HA and mutant HAs after 2 hours of chase at 37° C. revealed extensive differences in the rate at which the mutant HAs reached the cell surface at 37° C. Mutant 46+ became accessible to trypsin at a rate similar to that of the wild-type HA. while a larger proportion of the other mutant HAs remained inaccessible to trypsin at the end of the chase period. Mutant 476+ did not become accessible to trypsin after synthesis at 37° C. This result is consistent with its inefficient transport from the ER at 37° C.

(3) Effect of Temperature on the Addition of Supernumerary Oligosaccharide Side Chains and on the Intracellular Transport of Mutant HAs It has been observed that the extent of glycosylation at individual consensus sites can be affected by the temperature at which the protein is synthesized (Schuy, W. C. et al, *EMBO J.*, 5:2831-2836 (1986)), possibly due to alteration of the rate at which the nascent polypeptide folds into a conformation that masks the consensus sequence. As a result, the wild-type and mutant HAOs were analyzed after synthesis at either 30° C. or 42° C. Analysis of the biosynthesis of the wild-type and mutant HAs at 30° C. and 42° C. was carried out as described above for 37° C. with the following modifications. CV-1 cells were infected with the SV40-recombinant viruses and incubated at 37° C. for 36 to 40 hours. Before labelling, the infected cells were pre-incubated at either 30° C. for 2 hours or 42° C. for 30 minutes. During the labelling and chase periods, these temperatures were accurately maintained until cell extracts were prepared.

Examination of the mobilities of the HA species by 10% (w/v) SDS-polyacrylamide gel electrophoresis and autoradiography as described above revealed that there was very little effect of temperature on the use of the natural or supernumerary glycosylation sites on the wild-type or mutant HAs. The wild-type HA and mutants 46+, 54A+ and 54B+ migrated as single components under all circumstances. Although there appeared to be some minor variability in the efficiency of the use of the consensus sequences in the other mutants (188+, 225+ and 476+) at the different temperatures, as evidenced by the appearance of an additional minor component having a mobility corresponding to the addition of one extra or one less oligosaccharide, this minor component did not comprise more than a few percent of the HA molecules.

By contrast, alterations in the temperature had dramatic effects on the transport of the mutant HAs through the cell. That is, when the wild-type and mutant HAs were synthesized at 30° C., the majority of all of the labelled HAs became accessible to trypsin within 4 hours of chase. Most notably, 75% of the molecules of mutant 476+ moved to the plasma membrane where they were cleaved into HA1 and HA2 subunits. On the other hand, after synthesis at 42° C. only wild-type X-31 HA and two of the mutants (46+ and 225+) became accessible to trypsin after 2 hours of chase. The other mutants showed no evidence of processing to the higher molecular mass, terminally glycosylated form of HAO. This indicates that they were not transported from the ER at the higher temperature.

(4) Detection of Structural Alterations Resulting From the Addition of Additional N-linked Oligosaccharide Side Chains The introduction of amino acid changes that ultimately direct the addition of large post-translational modifications may well alter the native structure of HA. Structural alterations may arise as a consequence either of the substitution of the individual amino acid residues, or of the addition of the bulky N-linked glycan or a combination of these changes. Although it was attempted to minimize the structural effects by careful selection of the additional sites for N-linked oligosaccharide side chain attachment, any change in the location or global conformation of the mutant HAs was analyzed in the following manner.

Monoclonal antibodies prepared against wild-type X-31 HA were used as probes to detect any alterations in four major antigenic epitopes on the mutant HAs. Again, three of the antigenic epitopes (sites A, B and C) are located on the globular head of the molecule (see FIG. 2) and in general consist of exposed loops on the surface of the protein (Wiley, D. C. et al, *Nature*, 289:373-378 (1981). Antibodies specific for these sites have been observed to be relatively indifferent to changes in the global conformation of the HA molecule and to recognize both the monomeric and trimeric forms of the protein. However, the fourth epitope (site D) (see FIG. 2) maps in the trimer interface (Wiley, D. C. et al, *Nature*, 289:373-378 (1981) and appears to be displayed only when the molecule is in the fully folded trimeric form. Single amino acid changes, including those that result in the addition or the loss of an N-linked glycan, can alter or block recognition by monoclonal antibodies specific for these sites (Wiley, D. C. et al, *Ann. Rev. Biochem.* 56:365-395 (1987)). Because some of the antigenic epitopes may have been "masked" by the addition of novel N-linked oligosaccharide side chains within or near the epitope, binding of the antibodies to the mutant HAs was analyzed after synthesis of the mutant HAs both in the absence and presence of tunicamycin, again, a specific inhibitor of N-linked glycosylation (Schwarz, R. T. et al, *Trends Biochem. Sci.*, 5:65-67 (1980). Binding of the monoclonal antibodies to the glycosylated and non-glycosylated proteins was determined by immunoprecipitation of labelled HA as described above. The results are summarized in Table II below.

TABLE II

Effect of Temperature on the Antigenic Epitopes and Functional Activities of Wild-type and Mutant HAs

| | Assay Results at 37° C. | | | | | | Assay Results at 30° C. | | | | | |
|---|---|---|---|---|---|---|---|---|---|---|---|---|
| | Binding to mAbs | | | | RBC | Cell/cell | Binding to mAbs | | | | RBC | Cell/cell |
| | A | B | C | D | binding | fusion | A | B | C | D | binding | fusion |
| XHA | + | + | + | + | >90% | +++ | + | + | + | + | >70% | +++ |
| XHA46+ | + | + | + | + | >90% | +++ | + | + | + | + | >70% | +++ |
| XHA54A+ | + | + | + | − | >90% | +++ | + | + | + | + | >70% | +++ |
| XHA54B+ | + | + | ±* | − | >90% | +++ | + | + | ± | + | >70% | +++ |

TABLE II-continued Effect of Temperature on the Antigenic Epitopes and Functional Activities of Wild-type and Mutant HAs

| | Assay Results at 37° C. | | | | | | Assay Results at 30° C. | | | | | |
|---|---|---|---|---|---|---|---|---|---|---|---|---|
| | Binding to mAbs | | | | RBC | Cell/cell | Binding to mAbs | | | | RBC | Cell/cell |
| | A | B | C | D | binding | fusion | A | B | C | D | binding | fusion |
| XHA188+ | + | ± | + | − | 0% | +++ | + | + | + | + | 5% | +++ |
| XHA225+ | + | + | + | + | >90% | +++ | + | + | + | + | >70% | +++ |
| XHA476+ | + | + | + | − | 0% | − | + | + | + | + | >70% | +++ |

*± indicates weak recognition by the antibody.

Labelled proteins of the expected size (about 74–76 kD for the glycosylated molecules or 60 kD for the non-glycosylated molecules) could be immunoprecipitated from extracts of cells expressing the wild-type and mutant HAs using monoclonal antibodies specific for the A, B or C sites as well as by polyclonal anti-X-31 HA serum. Unfortunately, the affinity of the site D antibody appeared to be insufficient for immunoprecipitation of HA under the conditions employed, although it was suitable for use in immunofluorescence experiments described below. The majority of the mutants were recognized by all three A, B and C monoclonal antibodies. However, mutant 54B+ was only weakly recognized by the C monoclonal antibody, whether or not it was glycosylated. It is likely that this altered binding affinity may be due to the substitution of $Pro_{55}$ by Gly. In contrast, the B monoclonal antibody immunoprecipitated the non-glycosylated form of mutant 188+ although it only recognized the glycosylated form weakly at 37° C. This result indicates that residue 190 does not form part of the B antibody combining site since the substitution of $Glu_{190}$ by Ser to form the Asn-Gln-Ser consensus sequence did not prevent antibody binding in the absence of glycosylation. The weak recognition of the glycosylated protein could either result from shielding of the region by the N-linked oligosaccharide side chain or from modification of the ε-amino group of $Asn_{188}$. Substitution of this residue by aspartic acid has been observed in virus variants that escape neutralization by the B antibody (Wiley, D. C. et al, Ann. Rev. Biochem. 56:365–395 (1987)).

Next, indirect immunofluorescence of permeabilized cells was used to assay recognition of the wild-type and mutant HAs by the complete panel of monoclonal antibodies. More specifically, CV-1 cells expressing wild-type or mutant HAs grown on glass coverslips were rinsed three times with PBS and then fixed for 20 minutes with a 3.7% (v/v) solution of formaldehyde in PBS. The cells were then washed three times with PBS (one wash for a 10–20 minute duration) and then any remaining fixative was quenched with a 20 mM solution of ammonium chloride in PBS. After three rinses with PBS, the cells were permeabilized by treatment for 20 minutes with 0.1% (v/v) Triton X-100 (Sigma Chemical Co.) in PBS containing 0.25% (w/v) gelatin, then rinsed three times with PBS and washed two times for 10–20 minutes with PBS containing 0.25% (w/v) gelatin. The cells were then incubated at room temperature for 20 minutes in a moist chamber with 50 μl of a 1/500 or 1/1000 dilution, in PBS containing 0.25% (w/v) gelatin, of anti-HA antibody, rinsed three times with PBS containing 0.25% (w/v) gelatin and incubated at room temperature for 20 minutes in a moist chamber with 50 μl of a 1/1000 dilution, in PBS containing 0.25% (w/v) gelatin, of fluorescein isothiocyanate-conjugated goat anti-rabbit IgG or goat anti-mouse IgG (Cappel Labs.). Following three rinses with PBS containing 0.25% (w/v) gelatin, and three rinses with PBS, the cells were mounted in Moviol (Polysciences, Inc.) and examined using a fluorescence microscope. The results are summarized in Table II above.

Monoclonal antibody A recognized the wild-type HA and all of the mutant proteins, revealing fluorescent-staining patterns similar to those seen with the polyclonal antiserum. The patterns of recognition of the mutant HAs by the A, B and C monoclonal antibodies were consistent with those obtained above using immunoprecipitation. After synthesis at 37° C. only cells expressing the wild-type HA or mutants 46+ and 225+ displayed surface and internal fluorescence with monoclonal antibody D. However, when the HAs were synthesized and accumulated at 30° C., every mutant HA could be recognized by the D monoclonal antibody, yielding an intense cell surface and internal staining pattern. Since the D monoclonal antibody appears to recognize an epitope that is formed solely when the globular domains at the top of the HA molecules are packed together correctly (Wiley, D. C. et al, Nature, 289:373–378 (1981), it seems that only mutants 46+ and 225+ display the native trimeric structure at 37° C. However, all of the mutant HAs appear to be correctly folded and oligomerized at 30° C. since all were recognized by the D monoclonal antibody.

Conformational changes in HA have been shown to enhance its susceptibility to proteases, presumably by exposure of protease-sensitive sites which are inaccessible in the native protein (Skehel, J. J. et al, Proc. Natl. Acad. Sci. U.S.A., 79:968–972 (1982); and Doms, R. W. et al, J. Virol., 60:833–339 (1986). Monomeric or improperly folded forms of HA are degraded by trypsin, while correctly folded HA trimers are resistant to degradation by the protease although the HA molecules are cleaved into their component HA1 and HA2 subunits (Gething, M. J et al Cell, 46:939–950 (1986)).

Accordingly, the protease sensitivity of the wild-type and mutant HAs was determined by preparing cell extracts from CV-1 cells which were infected with the SV40-HA recombinant viruses as described above. The cells were labeled for 1 hour at 37° C. or 30° C. with 100 μCi per 250 μl of $^{35}S$-methionine (specific activity: 800 Ci/mmole). The cell extracts were prepared from infected cells using a lysis buffer lacking protease inhibitors. i.e., 50 mM Tris-HCl, pH 8.0, containing 1.0% (v/v) Nonidet P-40 and then incubated in the absence or in the presence of 25 μg/ml of trypsin for 15 min at 4° C. Thereafter, an excess (100 μg/ml) of soybean trypsin inhibitor was added and the cell extracts were immunoprecipitated using anti-HA polyclonal serum, subjected to 10% (w/v) SDS-polyacrylamide gel electrophoresis and autoradiographed as described above.

Mutant 476+ completely degraded by trypsin following synthesis at 37° C. This suggests that its structure is unfolded after synthesis at 37° C. By contrast, wild-type HA and the other mutant HAs were cleaved into HA1 and HA2 subunits that were completely or largely resistant to further digestion by the protease at 4° C. As discussed above, mutant 188+ displayed increased susceptibility to degradation by trypsin, although significant amounts of intact HA1 and HA2 subunits remained after digestion of the cell extract at 4° C.

After synthesis at 30° C., all of the mutant HAs, including 476+, were resistant to degradation by trypsin although they could be cleaved into stable HA1 and HA2 subunits. These results are consistent with all of the mutant HAs becoming folded into the correct trimeric structure at the lower temperature.

(5) Functional Activities of Wild-type and Mutant HAs

Functional X-31 HA displayed on the cell surface can be detected using an assay which reflects the receptor-binding activity of the molecule, i.e., the sialic binding activity of HA can be monitored by the hemagglutination of erythrocytes (red blood cells (hereinafter "RBC")) to infected cell monolayers (Gething, M. J. et al, Nature, 293:620–625 (1981)). Further, functional X-31 HA displayed on the cell surface can also be detected using an assay which reflects the membrane fusion activity of the molecule. These activities are involved in the infectious entry of influenza virions into the host cell (Gething, M. J. et al, In: Genetics of Influenza Viruses, Ed. Palese, P. et al, Springer-Verlag, Berlin, pages 169–191 (1983)).

Erythrocyte binding and cell fusion assays were carried out as described in White, J. et al, Nature, 300:658–659 (1982); and Gething, M. J. et al, J. Cell Biol., 102:11–23 (1986). More specifically, CV-1 cells, infected with the SV40-HA recombinant viruses as described above, were incubated at 37° C. for 36–60 hours before carrying out the assays. For studies of HAs synthesized at 30° C. the infected CV-1 cells were initially incubated at 37° C. for 18 hours, and just before the commencement of synthesis of HA, the infected cells were incubated at 30° C. for an additional 48 hours to ensure that all of the HA appearing and accumulating on the plasma membrane had been synthesized at 30° C.

The erythrocyte binding assay was carried out using infected CV-1 monolayers which had been incubated with guinea pig, chick or human RBCs (a 1.0% (v/v) solution in PBS for 15 minutes at room temperature). The CV-1 monolayers were then washed with PBS until all of the loose RBCs were removed and examined by light microscopy. The results are shown in Table II above.

As shown in Table II above, at 37° C., greater than 90% of the cells which expressed either the wild-type HA or mutants 46+, 54A+, 54B+ and 225+ bound erythrocytes densely. However, cells expressing two of the mutants (188+ and 476+) failed to bind erythrocytes following synthesis at 37° C. In the case of mutant 476+, this lack of binding is almost certainly the result of the failure to transport a sufficient amount of functional HA to the cell surface expression at 30° C. resulted in binding of erythrocytes to greater than 70% of cells. Lack of transport of the mutant protein cannot provide the explanation for the failure of the cells expressing mutant 188+ to bind significant numbers of erythrocytes because adequate levels of functional HA are present at the cell surface following synthesis at either temperature. It is likely that the supernumerary oligosaccharide masks the activity of the sialic acid binding receptor either by shielding or by disrupting the binding site.

CV-1 cells expressing HA on their plasma membranes can be induced to fuse with each other after brief exposure to low pH (White, J. et al, Nature, 300:658–659 (1982); and Gething, M. et al, J. Cell. Biol., 102:11–23 (1986)). This results in the formation of large syncytial cells and occurs within a defined pH range.

In order to analyze the ability of CV-1 cells infected with the SV40-HA recombinant viruses to fuse together to form polykaryons, the assay described by Gething, M. J. et al, J. Cell Biol., 102:11–23 (1986) was employed. More specifically, 54–60 hours after infection of CV-1 cells, when parallel cultures showed greater than 90% RBC binding, the infected CV-1 cells were treated with 5.0 µg/ml trypsin to cleave HAO into the HA1 and HA2 subunits. The CV-1 monolayers were then treated for 60 seconds at 37° C. with fusion medium comprising PBS containing 10 mM 2-(N-morpholino)ethane sulfonic acid and 10 mM HEPES adjusted to pH 5.5 or 5.9 with HCl or NaOH. The fusion medium was then removed and the cells were incubated for 5 to 8 hours in DMEM. At this time, the cells were fixed in ice-cold methanol, stained with Giemsa and examined by light microscopy. The results of these experiments and others performed following synthesis at 30° C. are also shown in Table II above.

As shown in Table II above, following synthesis at 37° C., only mutant 476+ failed to mediate cell fusion within a pH range between 5.0 to 5.8. However, when synthesized at 30° C., all of the mutant HAs mediated the fusion reaction with the same pH dependence as that displayed by the wild-type HA. The failure to transport a sufficient amount of functional HA to the cell surface at 37° C., provides the explanation for the lack of fusion of cells expressing mutant 476+. Further, the ability of mutant 188+ to mediate cell fusion despite its lack of hemagglutination activity demonstrates that binding of HA to sialic acid-containing residues on a target membrane is not a prerequisite for membrane fusion.

The above experiments demonstrate that in vivo oligonucleotide mutagenesis can be employed to produce transport-competent HA molecules containing additional N-linked oligosaccharide side chains that shield functional sites and epitopes. These experiments also evidence that the method of the present invention can be used as a general tool for shielding chosen areas of the surface of proteins that enter or traverse the exocytotic pathway and can be used to either pinpoint the location of functional sites or epitopes on the surface of a protein or to shield the activity of previously identified functional sites or epitopes.

EXAMPLE 2

In this example, a mutant t-PA that contains a supernumerary consensus sequence for glycosylation in addition to the three natural consensus sequences found on the wild-type t-PA protein has been constructed by oligonucleotide-directed mutagenesis in order to identify and shield the epitope or binding site on the surface of the t-PA molecule that interacts with a specific cellular receptor involved in the clearance of t-PA from the circulation in the liver.

Tissue plasminogen activator, an enzyme widely used as a thrombolytic agent in the treatment of acute myocardial infarction, does not dissolve blood clots directly. Instead, t-PA specifically cleaves a single peptide bond in plasminogen, thereby converting the inactive proenzyme into the powerful but non-specific protease, plasmin, which efficiently solubilizes the fibrin mesh that forms the core of the clot (Collen, D. *Thomb. Haemostasis*, 43:77-89 (1980)). The rate of activation of plasminogen by t-PA is accelerated by 2-3 orders of magnitude in the presence of polymerized fibrin, to which both plasminogen and t-PA bind (Hoylaerts, M. et al, *J. Biol. Chem.*, 257:2912-2919 (1982); Ranby, M., *Biochim. Biophys. Acta*, 704:461-469 (1982); and Rijken, D. C. et al, *J. Biol. Chem.*, 257:2920-2925 (1982)). This combination of properties leads to a preferential production of plasmin on the surface of the clot, where its activity will be most beneficial.

The amino acid sequence of the human t-PA precursor, deduced from the nucleotide sequence of cloned cDNAs (Pennica, D. et al, *Nature*, 301:214-221 (1983); and Harris, T. J. R. et al, *Mol. Biol. Med.*, 3:279-292 (1986)) is 563 residues in length, including a signal sequence of 20-23 hydrophobic amino acids and a hydrophilic "pro" sequence of 12-15 amino acids. Oligosaccharide groups are added at three potential glycosylation sites on the molecule and the signal and pro sequences are cleaved from the newly synthesized enzyme as it is transported along the secretory pathway (Pohl, G. et al, *Biochem.*, 23:3701-3707 (1984); Pohl, G. et al, *Eur. J. Biochem.*, 170:69-75 (1987); Vehar, G. A. et al, *Biotech.*, 2:1051-1057 (1984); and Sambrook, J. et al, *Mol. Biol. Med.*, 3:459-481 (1986)). t-PA is secreted from endothelial cells as a single polypeptide chain that is subsequently cleaved (between $Arg_{275}$ and $Ile_{276}$) into two chains held together by a single disulfide bond (Rijken, D. C. et al, *J. Biol. Chem.*, 256:7035-7041 (1981)). Both the single- and two-chain forms of the enzyme can bind to fibrin (Rijken, D. C. et al, *J. Biol. Chem.*, 257:2920-2925 (1982); Higgins, D. L. et al, *Biochem.*, 26:7786-7791 (1987)), although the two-chain form is catalytically more active (Wallen, P. et al, *Biochim. Biophys. Acta*, 719:318-328 (1982); Ranby, M., *Biochim. Biophys. Acta*, 704:461-469 (1982); Tate, K. M. et al, *Biochem.*, 26:338-343 (1987); and Petersen, L. C. et al, *Biochim. Biophys. Acta*, 952:245-254 (1988)). In addition, both forms of the enzyme (Jorgensen, M. et al, *Thromb. Haemostasis*, 58:872-878 (1987)) are inactivated by a fast-acting plasminogen activator inhibitor (PAI-1), a member of the serpin family that is secreted from endothelial cells and forms a covalent bond with $Ser_{478}$ of t-PA (Levin, E. G., *Proc. Natl. Acad. Sci. U.S.A.*, 80:6804-6808 (1983); and Sprengers, E. D. et al, *Blood*, 69:381-387 (1987)).

As shown in FIG. 3A, mature t-PA (527 amino acids) is organized by 16 disulfide bridges into a series of five discrete structural domains that are strikingly homologous to similar domains found in other secreted and cell surface proteins, including several serine proteases of plasma (Ny, T. et al, *Proc. Natl Acad. Sci. U.S.A.*, 81:5355-5359 (1984); and Patthy, L., *Cell*, 41:657-663 (1985)). Residues 4-50 of the mature protein form a "finger" domain (F), closely related to the fibrin-binding finger structures of fibronectin (Banyai, L. et al, *FEBS Lett.*, 163:37-41 (1983)). Residues 51-87 share homology with the precursor to epidermal growth factor (EGF) (Doolittle, R. F. et al, *Nature*, 307:558-560 (1984)) and with similar domains in a variety of other proteins, including urokinase (Verde, P. et al, *Proc. Natl. Acad. Sci. U.S.A.*, 81:4727-4731 (1984)), protein C (Foster, D. et al, *Proc. Natl. Acad, Sci. U.S.A.*, 81:4766-4770 (1984)), coagulation factors IX and X (Anson, D. S. et al, *EMBO J.*, 3:1053-1060 (1984)); and Leytus, S. P. et al, *Proc. Natl. Acad. Sci. U.S.A.*, 81:3699-3702 (1984)), the receptor for low-density lipoprotein (Russell, D. W. et al, *Cell*, 37:577-585 (1984)) and differentiation-specific proteins encoded by *Drosophila melanogaster* (Wharton, K. A. et al, *Cell*, 43:567-581 (1985)) and *Caenorrhabditis elegans* (Greenwald, I., *Cell*, 43:583-590 (1985)). This EGF-like domain is referred to as E. Residues 88-175 and 176-263 form two sequential "kringle" domains ($K_1$ and $K_2$), each built around three characteristic intradomain disulfide bonds (Olsson, G. et al, *FEBS Lett.*, 145:317-322 (1982); Park, C. et al, *Biochem.*, 25:3977-3982 (1986); and Holland, S. K. et al, *EMBO J.*, 6:1875-1880 (1987)). Domains of similar structure are found in plasminogen, prothrombin, urokinase and lipoprotein(a) (Patthy, L. et al, *FEBS Lett.*, 171:131-136 (1984); Patthy, L., *Cell*, 41:657-663 (1985); and McLean, J. W. et al, *Nature*, 330:132-137 (1987)). The remainder of the molecule (residues 277-527) constitutes the catalytic domain, which shares homology with other members of the serine protease family and contains a typical catalytic triad of amino acids ($His_{322}$, $Asp_{371}$ and $Ser_{478}$).

Exogenously administered t-PA is capable of eliciting prompt thrombolysis in therapeutic doses that do not produce marked fibrinogenolysis in experimental animals with induced coronary artery thrombosis (Bergmann, S. R. et al, *Science*, 220:1181-1183 (1983)) and in patients with evolving myocardial infarction (Van de Werf, F. et al, *New Eng. J. Med.*, 310:609-613 (1984); Collen, D. et al, *Circ.*, 70:1012-1017 (1984); Van de Werf, F. et al, *Circ.*, 69:605-610 (1984); Thrombolysis in Myocardial Infarction Study Group, *New Eng. J. Med.*, 312:932-936 (1985); and European Cooperative Study Group, *Lancet*, 1:842-847 (1985)). However, because the clearance of t-PA from the circulation is so rapid, continuous infusions have been required. In the several animal species studied (Nilsson, T. et al, *Scand J. Haematol.*, 33:49-53 (1984); Devries, S. R. et al, *Fibrin.*, 1:17-21 (1987); Korninger, C. et al, *Thromb. Haemostasis*, 46:658-661 (1981); Bounameaux, H. et al, *Blood*, 67:1493-1497 (1986); Beebe, D. P. et al, *Thromb. Res.*, 43:663-674 (1986); Nilsson, S. et al, *Thromb. Res.*, 39:511-521 (1985); Emeis, J. J. et al, *Thromb. Haemost.*, 54:661-664 (1985); Rijken, D. C. et al, *Biochem. J.*, 238:643-646 (1986); and Fuchs, H. E. et al, *Blood*, 65:539-544 (1985)) the half-life of t-PA in the circulation varies approximately inversely with the logarithm of body weight and ranges from 2-3 minutes in mouse to 5-10 minutes in man (Bounameaux, H. et al, In: *Thrombolysis: Biological and Therapeutic Properties of New Thrombolytic Agents*, Ed. Collen, D. et al, Churchill Livingstone, Edinburgh, pages 85-91 (1985)). At present, t-PA is administered clinically in the form of an initial bolus that is followed by sustained infusion. The total amount of enzyme administered during a standard 3 hour treatment is 50-100 mg. Such large amounts are required for two reasons: first, to counterbalance the effects of the rapid clearance of t-PA from the circulation, and second, to overcome the effects of high concentrations of fast-acting inhibitors of the enzyme that are present in plasma and platelets.

The liver appears to be the major site of removal and catabolism of t-PA (Nilsson, T. et al, *Scand. J. Haematol.*, 33:49-53 (1984); Devries, S. R. et al, *Fibrin.*, 1:17-21 (1987); Korninger, C. et al, *Thromb. Haemostasis*, 46:658-661 (1981); Bounameaux, H. et al, *Blood*, 67:1493-1497 (1986); Beebe, D. P. et al, *Thromb. Res.*, 43:663-674 (1986); Nilsson, S. et al, *Thromb. Res.*, 39:511–521 (1985); Emeis, J. J. et al, *Thromb Haemost.*, 54:661–664 (1985); Rijken, D. C. et al, *Biochem. J.*, 238:643–646 (1986); and Fuchs, H. E. et al, *Blood*, 65:539–544 (1985)). Exogenous t-PA delivered intravascularly rapidly accumulates in liver and is subsequently degraded. Further, the half-life of circulating t-PA is markedly prolonged in animals subjected to hepatectomy (Bounameaux, H. et al, *Blood*, 67:1493–1497 (1986); and Nilsson, T. et al, *Scand. J. Haematol.*, 33:49–53 (1984)). Neither the protease active site nor a specific glycosylation pattern appears to be a major determinant of hepatic recognition and degradation of t-PA in vivo (Fuchs, H. E. et al, *Blood*, 65:539–544 (1985)), in perfused liver systems (Emeis, J. J. et al, *Thromb. Haemost.*, 54:661–664 (1985)), or in isolated hepatocytes (Bakhit, C. et al, *J. Biol. Chem.*, 262:8716–8720 (1987). The clearance and catabolism of t-PA has been reviewed in detail (Krause, J. *Fibrin.*, 2:133–142 (1988)). However, information is limited regarding the particular cell type responsible for clearance of t-PA. Both the rapid clearance of t-PA from the circulation and its accumulation in the liver are best explained by the existence of a high affinity uptake system for t-PA on hepatocytes. It is believed that this very efficient uptake system might consist of one or even different types of specific hepatic receptors, although to date, no protein resembling such a receptor has been identified and characterized. After administration of fluorescent or radiolabeled t-PA to rats and subfractionation of the livers into parenchymal, endothelial, and Kupffer cells, it was found that parenchymal and endothelial cells constitute the major sites for hepatic uptake (Sprengers, E. D. et al, *Blood*, 69:381–387 (1987); and Kuiper, J. et al, *Fibrin*, 2:28 (1988)). The uptake of t-PA into all liver cell types is inhibited by in vivo competition with unlabelled t-PA. whereas glycoproteins such as mannan and ovalbumin inhibit the specific uptake of labelled t-PA in isolated liver endothelial cells. This indicates that the endocytosis of t-PA is mediated, at least in part, by mannose receptors on endothelial cells (Einarsson, M. et al, *Thromb. Haemost.*, 54:270 (1985); and Kuiper, J. et al, *Fibrin.*, 2:28 (1988)). Monensin, $NH_4Cl$, and cytochalasin B block the uptake and degradation of t-PA, indicating that the uptake is endocytotic and that the degradation is lysosomal. In hepatoma cell lines, representing parenchymal cells, t-PA clearance involves ligand binding, uptake, and degradation mediated by a novel high-capacity, high-affinity specific receptor system (Owensby, D. A. et al, *J. Biol. Chem.*, 263:10587–10594 (1988).

Recent studies have indicated that the mannose-rich oligosaccharide attached to $Asn_{117}$ on t-PA is the major structure recognized for clearance via mannose-dependent receptors on liver endothelial cells (Hotchkiss, C. et al, *Fibrin.*, 2:30 (1988)) which appears to constitute approximately 30% of the total liver uptake (Kuiper, J. et al, *Fibrin.*, 2:28 (1988)). Approximately 60% of the t-PA uptake in the liver appears to involve the specific t-PA receptor on parenchymal cells (Kuiper, J. et al, *Fibrin.*, 2:28 (1988)).

The structure on t-PA that is recognized by the specific receptor has not yet been defined although studies using t-PA domain deletion mutants have indicated that sequences within the EGF-like domain and/or the finger domain might be involved (Collen, D. et al, *Blood*, 71:216–219 (1988); Browne, M. J. et al, *J. Biol. Chem.*, 263:1599–1602 (1988); Kalyan, N. K. et al, *J. Biol. Chem.*, 263:3971–3978 (1988); Robinson, J. H. et al, *Fibrin.*, 2:31 (1988)). The related plasminogen activator, urokinase (hereinafter "u-PA"), has been shown to bind to a different specific cell surface receptor (Neilsen, L. S. et al, *J. Biol. Chem.*, 263:2358–2363 (1988)) and it has been demonstrated that the receptor binding domain on u-PA is located within the EGF-like domain of that molecule (Appella, E. et al, *J. Biol. Chem.*, 262:4437–4440 (1987)) within the same stretch of residues (19–31) that are involved in the binding of EGF to its own receptor (Komoriya, A. et al, *Proc. Natl. Acad. Sci. U.S.A.*, 81:1351–1355 (1984); Heath, W. F. et al, *Proc. Natl. Acad. Sci. U.S.A.*, 83:6367–6371 (1986); De Marco, A. et al, *J. Biol. Chem.*, 261:13510–13516 (1986)). It was therefore postulated in the present invention that the homologous region of t-PA might be responsible for binding to its specific hepatic cell receptor. To analyze this possibility, oligonucleotide-directed mutagenesis has been employed in the present invention so as to introduce a nucleotide substitution into a cloned copy of the gene encoding t-PA such that a new consensus sequence for attachment of an N-linked oligosaccharide side chain is introduced within the EGF-like domain of the t-PA molecule. This example describes the construction and characterization of the mutant t-PA and demonstrates that the addition of the N-linked oligosaccharide side chain shields the hepatic cell receptor binding site on the t-PA molecule.

A. Selection of the Site for the Introduction of the Consensus Sequence

The 3-dimensional structure of the t-PA molecule is not known. However, the solution structures of the human and murine EGF molecules have been defined using NMR (Montelione, G. T. et al, *Proc. Natl. Acad. Sci. U.S.A.*, 83:8594–8598 (1986); Montelione, G. T. et al, *Proc. Natl. Acad. Sci. U.S.A.*, 84:5226–5230 (1987); Cooke, R. M. et al, *Nature*, 327:339–341 (1987)). The structure of the EGF-like domain of t-PA is postulated in the present invention to be very similar since the positions of the three disulfide bonds are absolutely conserved in all of the homologous structures. Mapping of the amino acid sequence of the EGF-like domain of t-PA onto the EGF structure reveals that $Tyr_{67}$, which lies two amino acids upstream of a Ser residue (see FIG. 3A), would be positioned on a turn linking the two strands of the major $\beta$-sheet of the structure and is very likely to be exposed on the surface of the folded domain. A single nucleotide substitution in the TAC codon specifying $Tyr_{67}$ can generate the AAC codon specifying Asn, resulting in the generation of a new Asn-Phe-Ser consensus sequence for N-linked glycosylation in the EGF-like domain (see FIG. 3B). $Tyr_{67}$ corresponds to $Glu_{25}$ of EGF and $Tyr_{24}$ of $\mu$-PA, both of which lie within stretches of residues (19–31) reported to bind to the respective specific hepatic cell receptors (De Marco, A. et al, *J. Biol. Chem.*, 261:13510–13516 (1986); Appella, E. et al, *J. Biol. Chem.*, 262:4437–4440 (1987)). Thus, the new glycosylation site on the EGF-like domain of t-PA would lie within this putative hepatic cell receptor binding site.

B. Oligonucleotide Mutagenesis

A full length cDNA copy of the mRNA encoding t-PA was constructed as described in Sambrook, J. et al, *Mol. Biol. Med.*, 3:459–481 (1986). Unless otherwise specified, the techniques used in this construction, i.e., purification of mRNA, cDNA cloning, preparation of plasmid DNA, digestion with restriction enzymes, agarose gel electrophoresis of DNA, transfer of DNA to nitrocellulose and hybridization, radiolabeling of DNA by nick-translation, ligation, addition of synthetic linkers and bacterial transformation were carried out as described by standard methods (Maniatis, T. et al, *Molecular Cloning*, Cold Spring Harbor (1982)).

More specifically, polyadenylated mRNA, isolated from the Bowes line of melanoma cells, was used as a template for synthesis of double-stranded cDNA. The double-stranded cDNA was introduced into bacterial plasmids by the addition of homopolymeric dG.dC tails or by the sequential addition of EcoRI synthetic linkers at the 3' end and SalI synthetic linkers at and the 5' end (Helfman, D. M. et al, *Proc. Natl. Acad. Sci. U.S.A.*, 80:31–35 (1983)). The resulting cDNA libraries were screened by hybridization to $^{32}$P-labeled oligonucleotide probes (a pool of 24 different 17-mers) prepared from the deduced amino acid sequence of the amino terminus of mature t-PA (purified from Bowes melanoma cell conditioned medium). Three overlapping cDNA sequences spanning the entire coding sequence and portions of the untranslated 5' and 3' sequences were joined by ligation at two naturally occurring internal EcoRI sites to generate a contiguous segment encoding the entire t-PA molecule. During cloning of t-PA cDNA, a SalI site was introduced into the 5' untranslated region of the molecule (125 base pairs upstream from the initiator codon). A naturally occurring BglII site is located in the 3' untranslated region of the t-PA cDNA (391 base pairs downstream from the termination codon). Following partial digestion of the t-PA cDNA with BglII. the resulting recessed 3' ends were filled with the Klenow fragment of DNA polymerase I. The cDNA was then digested to completion with SalI and the resulting t-PA fragment was cloned into the SalI and blunt-ended ClaI sites of a derivative of pBR322 to yield the plasmid pJ205 (Sambrook, J. et al, *Mol. Biol. Med.*, 3:459–481 (1986); provided by Genetics Institute, Boston, Mass.). Cleavage of pJ205 with SalI and HindIII releases a fragment of 2210 base pairs encoding the full-length t-PA cDNA.

Plasmid L611 contains a truncated version of the t-PA cDNA that lacks all of the 5' untranslated sequences, i.e., the sequences between the SalI site and the initiating ATG codon (Sambrook, J. et al, *Mol. Biol. Med.*, 3:459–481 (1986); provided by Genetics Institute, Boston, Mass.). Immediately upstream from the initiating AUG codon, plasmid L611 contains a synthetic oligonucleotide that introduces cleavage sites for BamHI and NcoI. Approximately 280 base pairs downstream of the TGA termination codon, a BalI site lies within the 3' untranslated sequence of the t-PA cDNA. XbaI linkers were then added to the approximately 1965 base pair NcoI-BalI fragment of t-PA DNA that was excised from plasmid pL611. This NcoI-BalI fragment therefore contains the sequences that code for the complete t-PA protein but lacks sequences corresponding to (i) the distal 3'-untranslated region of t-PA mRNA and (ii) all of the 5'-untranslated sequences of t-PA mRNA, i.e., the sequences between the SalI site and the initiating ATG codon (Pennica, D. et al, *Nature*, 301:214–221 (1983)). The fragment of t-PA cDNA carrying XbaI sites at each end was inserted into the pSVT7 expression vector (Bird, P. M. et al, *J. Cell Biol.*, 105:2905–2914 (1987)) to yield pSVTXPA. The correct orientation in the pSVTXPA vector of the t-PA XbaI fragment was confirmed by restriction endonuclease digestion.

pSVT7 was constructed from pKC3. pKC3 is a derivative of pko (Van Doren, K. et al, *J. Virol.*, 50:606–614 (1984)) in which the pBR322-derived sequences from the AvaI site to the EcoRI site (which contain the origin of replication and the beta-lactamase gene) have been replaced by those of pUC 8 (Messing, J., *Meth. Enzymol.*, 101:20–78 (1983)). In addition, a polylinker containing an XbaI site has been inserted into the unique HindIII site and the PvuII site upstream of the SV40 origin has been converted into a ClaI site. The vector pSVT7 was obtained by inserting a 20 base pairs fragment containing a bacteriophage T7 RNA polymerase-specific promoter (Pharmacia Fine Chemicals, Piscataway, N.J.) into the unique StuI site of pKC3. This StuI site lies within sequences derived from the early region of SV40 at nucleotide 5190 in the SV40 sequence and approximately 30 base pairs downstream from the point of initiation of the early transcript (Tooze, J., *DNA Tumor Viruses*, Cold Spring Harbor Press, page 813 (1981)).

In order to carry out oligonucleotide directed mutagenesis of the t-PA sequence, the XbaI fragment of t-PA cDNA was then ligated with replicative-form DNA of the bacteriophage M13 vector M13mp18 (Yanisch-Perron, C. et al, *Gene*, 33:103–119 (1985)) that had been digested with XbaI and subsequently dephosphorylated with calf intestinal alkaline phosphatase.

Unless otherwise specified, these and other standard recombinant DNA procedures described herein were carried out as described in (i) Maniatis, T. et al, *Molecular Cloning*, Cold Spring Harbor (1982) and (ii) *Meth. Enzymol.*, Volume 152, Ed. Berger, S. et al, Academic Press, New York (1987).

The ligated DNA was transfected into *E. coli* strain TG-1 (Gibson, T., Thesis, University of Cambridge, England (1984)). Plaques formed by recombinant bacteriophages were identified by hybridization to $^{32}$P labeled t-PA and single-stranded DNA was isolated. Mutations were introduced by two-primer mutagenesis using a universal sequencing primer (TGACCG-GCAGCAAAATG) (New England Biolabs, Beverly, Mass.) and the 5' phosphorylated mutagenic primer shown in FIG. 3B. which contains an adenine residue at position 388 (using the numbering system of Pennica, D. et al, *Nature*, 301:214–221 (1983)) in place of the wild-type thymine residue. The procedures used to carry out oligonucleotide mutagenesis and identification of the desired mutants are well known in the art and are described in detail in Zoller, M. et al, *Meth. Enzymol.*, 100:468–500 (1983); Zoller, M. et al, *DNA*, 3:479–488 (1984); and Doyle, C. et al, *J. Cell Biol.*, 103:1193–1204 (1986).

Once the desired base substitution had been confirmed, the double-stranded replicative form of the recombinant phage DNA containing the mutant t-PA sequence was prepared and purified by centrifugation on a CsCl$_2$-Ethidium bromide isopycnic gradient as described by Zoller, M. et al, *DNA*, 3:479–488 (1984) and digested with BglII and StuI. The approximately 1.26 kilobase pair BglII-StuI fragment containing the mutation was purified by agarose gel electrophoresis as described above. The corresponding approximately 1.26 kilobase pair BglII-StuI fragment containing the wild-type t-PA sequence was also removed from pSVTXPA by restriction endonuclease digestion and agarose gel electrophoresis and the remaining linear BglII-StuI fragment of plasmid DNA was purified and ligated to the BglII-StuI fragment containing the mutation to generate vector pSVTXPA67+ containing the full length mutant t-PA cDNA. pSVTXPA67+ transfected in E. coli DH-1 gave rise to the strain pSVTXPA67+ (DH-1) which has been deposited at the American Type Culture Collection under ATCC No. 67859. After transformation of E. coli DH-1 with pSVTXPA67+, plasmid DNA was prepared and the insertion of the mutated sequence was confirmed by restriction endonuclease digestion and by hybridization to the radiolabeled mutagenic oligonucleotide.

For analysis of the phenotype of the mutant t-PA, the wild-type and mutant t-PAs were expressed following transfection of pSVTXPA and pSVTXPA67+ plasmid DNAs into COS cells. More specifically, approximately $10^6$ COS cells (Gluzman, Y., Cell, 23:175–182 (1981)) per 100 mm dish were transfected with 5.0 µg of the appropriate plasmid DNA purified by alkaline extraction (Maniatis, T. et al, Molecular Cloning, Cold Spring Harbor (1982)). The medium was removed from the cells by aspiration and the monolayers were washed once with 5.0 ml of Dulbecco's medium (GIBCO, Inc.) containing 10 mM HEPES (pH 7.15) (Sigma Chemical Co.). After removal of the wash solution, the DNA was then added to the monolayers in a volume of 1.5 ml of wash solution containing 300 µg of DEAE-dextran (Pharmacia, Inc.). The monolayers were then incubated for 1 hour at 37° C. in an humidified atmosphere containing 6% $CO_2$. The monolayers were agitated gently every 20 minutes during this period. After the monolayers had been exposed to DNA for 1 hour, they were washed once with Dulbecco's medium containing HEPES (pH 7.15) and then 10 ml of Dulbecco's medium containing 10% (v/v) fetal bovine serum (GIBCO, Inc.) and 100 µM chloroquine (Sigma Chemical Co.) was added. The monolayers were then incubated for 4 hours as described above, washed twice with 5.0 ml of Dulbecco's medium lacking bovine serum albumin but containing 10 mM HEPES (pH 7.15). 10 ml of Dulbecco's medium containing 10% (v/v) fetal bovine serum was then added and the monolayers were incubated at 37° C. as described above for 12 hours. At this time, the monolayers were washed three times each with 5.0 ml Dulbecco's medium lacking bovine serum albumin and then incubated at 37° C. in the same medium for a further 36–60 hours. Mock-transfected cells were treated identically except that DNA was omitted from the solution containing DEAE-dextran. At the end of the incubation period, the supernatant medium was collected from the cells and the t-PA analyzed as described below.

C. Analysis of the Biosynthesis and Phenotype of Wild-Type and Mutant t-PAs

To determine whether the introduced consensus sequence was recognized as an additional site for N-linked glycosylation of the nascent t-PA polypeptide chain, the mobility of glycosylated and non-glycosylated forms of the wild-type and mutant t-PAs were compared by SDS-polyacrylamide gel electrophoresis. More specifically, approximately $10^6$ COS cells transfected with pSVTXPA67+ or pSVTXPA DNA as described above were labeled with $^{35}$S-cysteine and $^{35}$S-methionine from 50–52.5 hours post-transfection in the presence or absence of tunicamycin which blocks N-linked glycosylation. For 2 hours prior to labeling, at 48 hours post-transfection, the cells were preincubated in DMEM lacking methionine and cysteine and where appropriate, containing tunicamycin at 4.0 µg/ml. The cells were then labeled for 2.5 hours at 37° C. with 100 µCi per ml of $^{35}$S-methionine (specific activity: 800 Ci/mmole) and 150 µCi per ml of $^{35}$S-cysteine (specific activity: 1,000 Ci/mmole) in the absence or presence of 4.0 µg/ml tunicamycin in DMEM lacking methionine and cysteine. The medium containing labeled t-PA secreted from the cells was then collected and immunoprecipitated as described by Gething, M. J. et al, Cell, 46:939–950 (1986) using a polyclonal goat anti-human t-PA antiserum (American Diagnostica, Inc.). The immunoprecipitated proteins were then separated by electrophoresis on 8.0% (w/v) SDS-polyacrylamide gels (Laemmli, U. K., Nature, 227:680–685 (1970)) and visualized by autoradiography (Hahn, E. J., American Laboratory, July 1983).

The autoradiography showed that the t-PA67+ mutant migrated more slowly than the wild-type t-PA, with an increase in apparent molecular weight that is consistent with the presence of one additional N-linked oligosaccharide side chain. Non-glycosylated forms of the wild-type and mutant t-PAs synthesized in the presence of tunicamycin migrated with identical apparent molecular weights. Thus, the differences in mobility of the t-PA species reflect changes in the complement of N-linked oligosaccharide side chains rather than alterations in the polypeptide backbone.

To determine the effect of the supernumerary oligosaccharide on the enzymatic activity of the t-PA molecule, the wild-type and mutant t-PAs were purified from the medium collected from transfected cells using the immunoaffinity procedure described by Einarrson, M. et al, Biochim. Biophys. Acta, 830:1–10 (1985). The concentrations of t-PA in the purified preparations were quantitated by a solid-phase radioimmunoassay using the IgG fraction of a polyclonal goat anti-human t-PA antiserum (American Diagnostica, Inc.) and performed essentially as described for influenza HA (Gething, M. J. et al, Nature, 293:620–625 (1981)). The enzymatic activity of the wild-type and mutant t-PAs was then measured by an indirect chromogenic assay in which the free p-nitroaniline is released from the chromogenic substrate Spectrozyme PL (H-D-norleucyl-hexahydrotyrosyl-lysine-p-nitroanilide diacetate salt) (American Diagnostica, Inc.)) by the action of plasmin generated by the action of t-PA on plasminogen. The release of free p-nitroaniline was measured spectrophotometrically at 405 nm. More specifically, 100 µl reaction mixtures comprising 150–200 pg of the t-PA to be tested, 0.4 mM Spectrozyme PL, 0.01–0.16 µM of Lys-plasminogen (American Diagnostica, Inc.) and 0.5–25 µg/ml of soluble fibrin (American Diagnostica, Inc.) in a buffer comprising 50 mM Tris-HCl (pH 7.5), 0.1M NaCl, 1.0 mM EDTA and 0.01% (v/v) Tween 80 were prepared. Assays were performed at 37° C. in 96-well, flat-bottomed microtiter plates (Costar, Inc.), and $OD_{405nm}$ was measured with a Bio-tek microplate reader (Model EL310) at 15 or 30 minute intervals over a 2 hour period. Aliquots of buffer or appropriately-diluted samples of medium from mock-transfected cells were analyzed as controls and the OD values obtained (<0.01 unit) were subtracted from the corresponding test values. Delta OD values were measured as the change in optical density between 30 minutes and 60 minutes (i.e., following the lag phase of the reaction and the complete conversion of single-chain t-PA to the two-chain form). Under the conditions used in the standard assay (0.1 μM of Lys-plasminogen and 25 μg/ml of DESAFIB), the soluble fibrin stimulated the activity of wild-type t-PA 20- to 40-fold.

Using the standard assay conditions, the activity of the t-PA67+ mutant was approximately 60–70% that of the wild-type enzyme. When assays were performed over the range of substrate and soluble fibrin concentrations, it was determined that the $K_m$ of the mutant t-PA for Lys-plasminogen was approximately 2- to 4-fold higher than that of wild-type t-PA. The stimulation of the mutant t-PA by soluble fibrin was reduced at low DESAFIB concentrations but approached that of the wild-type enzyme at saturating levels of DESAFIB, i.e., 25 μg/ml. Although the kinetic parameters of the mutant t-PA are somewhat altered from those of the wild-type t-PA, the mutant t-PA is still a very effective fibrin-dependent plasminogen activator.

Finally, to determine whether the supernumerary N-linked oligosaccharide shields the hepatic cell receptor binding site on the t-PA molecule, the ability of metabolically-labeled wild-type and mutant t-PAs to bind to specific t-PA receptors on the H4 rat hepatoma cell line (Owensby, D. A. et al, *J. Biol. Chem.*, 263:10587–10594 (1988)) was compared. More specifically, $^{35}$S-labeled glycosylated or non-glycosylated t-PA and t-PA67+ proteins were prepared as described above and stored on ice. Approximately $2 \times 10^6$ H4-II-E cells (ATCC No. CRL 1548) growing in a monolayer on 60 mm diameter dishes were preincubated in DMEM lacking bovine serum albumin for 4 hours at 37° C. in a humidified atmosphere containing 6% $CO_2$. The cells were then washed with ice-cold DMEM and incubated in 4.0 ml of ice-cold DMEM containing 4.0 mg/ml bovine serum albumin (Type V from Sigma Chemical Co.) for 30 minutes on ice in a 5° C. cold room. The DMEM/bovine serum albumin was removed and the $^{35}$S-labeled t-PAs were added to the H4 cell monolayers (0.3 ml of each from the original 1.0 ml of supernatant medium, pre-chilled) and the cells were left on ice with occasional rocking for 2 hours. The medium was then removed from each monolayer (post-binding media). the monolayers were washed six times with 1.0 ml of 25 mM Tris-HCl (pH 7.4) containing 140 mM NaCl and 4.0 mg/ml bovine serum albumin, and then the cells were lysed in 0.3 ml of 1.0% (v/v) Nonidet P-40 lysis buffer as described above. The labeled t-PAs contained in the 0.3 ml samples of pre-binding media, post-binding media and the cell lysates were collected by immunoprecipitation as described above and then quantitated by autoradiography following separation on 8.0% (w/v) SDS-polyacrylamide gels.

The results of the autoradiography showed that a small but significant amount (5–10%) of the wild-type t-PA bound to the H4 cells. However, the t-PA67+ mutant containing a supernumerary N-linked oligosaccharide attached to the EGF-like domain was completely unable to bind to the H4 cells. That the abolition of binding was the result of the presence of the supernumerary oligosaccharide was demonstrated by the observation that the H4 cells bound equivalent amounts of the non-glycosylated forms (synthesized in the presence of tunicamycin) of both the wild-type and mutant t-PAs.

These results demonstrate that the presence of the supernumerary oligosaccharide attached at residue 67 of the EGF-like domain can shield or disrupt the hepatic cell receptor binding site on the t-PA molecule. Although the results are consistent with the localization of the hepatic cell receptor binding site within the stretch of residues surrounding residue 67, it is possible that the supernumerary oligosaccharide shields a binding site nearby on the molecule. Since the approximate location of the binding site has been localized, the specific residues involved in hepatic cell receptor binding can be delineated by substitution of individual amino acids as discussed above.

The prevention of binding of t-PA to specific cell surface receptors is believed to provide a significant advantage in clinical use, since the rate of clearance of t-PA from the circulation following administration should be significantly reduced. The consequent improvement in efficiency of thrombolysis should allow t-PA to be administered in much smaller doses than are currently required. Furthermore, because this t-PA67+ mutant contains only a single amino acid substitution in the wild-type t-PA protein sequence, which itself would be shielded by the presence of an N-linked oligosaccharide side chain, the protein is unlikely to elicit an antigenic response or be significantly different in structure from the wild-type t-PA. In these respects, this mutant t-PA is believed to have significant advantages over the known t-PA domain-deletion mutants that are more slowly cleared from the circulation than the wild-type t-PA (Krause, J., *Fibrin.*, 2:133–144 (1988)).

While the invention has been described in detail and with reference to specific embodiments thereof, it will be apparent to one skilled in the art that various changes and modifications can be made therein without departing from the spirit and scope thereof.

We claim:

1. A method for identifying or shielding functional sites or epitopes of a transportable protein comprising:
    (1) carrying out oligonucleotide-directed mutagenesis of selected nucleotides of the gene encoding said transportable protein so as to introduce DNA sequences encoding additional consensus amino acid sequence(s) for N-linked glycosylation by effecting a single amino acid mutation(s) on the exposed surface of said transportable protein;
    (2) transforming a eukaryotic cell with the resulting modified gene, wherein said eukaryotic cell expresses said modified gene and glycosylates said additional consensus amino acid sequence(s) so as to introduce additional N-linked oligosaccharide side chain(s) attached to asparagine residue(s) of the additional consensus amino acid sequence(s) located on the exposed surface of said transportable protein;
    (3) assaying the resulting modified transportable protein so as to determine if it possesses correct protein folding, wherein when correct protein folding has been confirmed;
    (4) assaying the modified transportable protein for inhibition of functional or epitopic activity so as to identify or confirm the shielding of the functional sites or epitopes, respectively, of said transportable protein.

2. The method as claimed in claim 1, wherein said transportable protein is a membrane protein.

3. The method as claimed in claim 2, wherein said membrane protein is selected from the group consisting of an enzyme, a receptor, a transport protein, and a cell surface antigen.

4. The method as claimed in claim 1, wherein said transportable protein is a secretory protein.

5. The method as claimed in claim 4, wherein said secretory protein is selected from the group consisting of an enzyme, an enzyme inhibitor, a cell attachment protein, a hormone, a growth factor and a carrier protein.

6. The method as claimed in claim 1, wherein said transportable protein is a genetically engineered transportable protein.

* * * * *